United States Patent
Cizeau et al.

(10) Patent No.: US 8,318,472 B2
(45) Date of Patent: Nov. 27, 2012

(54) OPTIMIZED NUCLEIC ACID SEQUENCES FOR THE EXPRESSION OF VB4-845

(75) Inventors: Jeannick Cizeau, Winnipeg (CA); Glen MacDonald, Winnipeg (CA); Arjune Premsukh, Winnipeg (CA)

(73) Assignee: Viventia Biotechnologies Inc., Mississauga, Ontario (CA)

( * ) Notice: Subject to any disclaimer, the term of this patent is extended or adjusted under 35 U.S.C. 154(b) by 144 days.

(21) Appl. No.: 12/679,963

(22) PCT Filed: Sep. 26, 2008

(86) PCT No.: PCT/CA2008/001680
§ 371 (c)(1),
(2), (4) Date: Jun. 24, 2010

(87) PCT Pub. No.: WO2009/039630
PCT Pub. Date: Apr. 2, 2009

(65) Prior Publication Data
US 2010/0267086 A1 Oct. 21, 2010

Related U.S. Application Data

(60) Provisional application No. 60/975,718, filed on Sep. 27, 2007.

(51) Int. Cl.
| *C12N 5/10* | (2006.01) |
| *C12N 15/13* | (2006.01) |
| *C12N 15/11* | (2006.01) |
| *C12N 15/62* | (2006.01) |
| *C07K 16/28* | (2006.01) |
| *C07K 16/46* | (2006.01) |

(52) U.S. Cl. ............... 435/252.33; 536/23.1; 536/23.53; 536/23.7; 435/320.1; 435/252.3; 435/254.11; 435/326; 435/328; 435/69.1; 435/69.7

(58) Field of Classification Search .................. None
See application file for complete search history.

(56) References Cited

U.S. PATENT DOCUMENTS

| 5,082,767 | A * | 1/1992 | Hatfield et al. |
| 6,339,070 | B1 * | 1/2002 | Emery et al. |
| 7,655,437 | B2 * | 2/2010 | Jevsevar et al. |
| 2003/0148950 | A1 * | 8/2003 | Xin et al. |
| 2007/0196366 | A1 * | 8/2007 | Zangemeister-Wittke et al. |

FOREIGN PATENT DOCUMENTS

| WO | WO 98/55623 A1 | 12/1998 |
| WO | WO 9965521 A1 * | 12/1999 |
| WO | WO2004/096271 | 11/2004 |
| WO | WO 2005/090579 A1 | 9/2005 |
| WO | WO 2005/121341 A1 | 12/2005 |

OTHER PUBLICATIONS

Gheradi et al., Structural basis of haptocyte growth factor/scatter factor and MET signalling, Proc. Nat. Acad. Sci. USA, 103(11):4046-4051, Mar. 14, 2006.*
International Search Report of PCT/CA2008/001680, Jan. 29, 2009.
Written Opinion of PCT/CA2008/001680 mailed Jan. 29, 2009.

* cited by examiner

*Primary Examiner* — Claire Kaufman
(74) *Attorney, Agent, or Firm* — Bereskin & Parr LLP/S.E.N.C.R.L., s.r.l.; Micheline Gravelle

(57) ABSTRACT

An optimized nucleic acid sequence encoding the immunoconjugate VB4-845 is disclosed. Modifications to the original VB4-845 nucleic acid sequence include optimization of the sequences encoding the $V_H$ region, $V_L$ region, linkers and pseudomonas exotoxin A. The modifications improved the yield of VB4-845 in an *Escherichia coli* expression system.

**26 Claims, 16

Figure 1: Original VB4-845 Nucleotide and Amino Acid Sequences (SEQ ID NOS: 1 and 2)

```
GAA TTC CTG CAG GTC TAT GGA ACG ATA AAT GCC CAT GAA AAT TCT ATT TCA AGG
                                                                RBS Site AGA CAG TCA TA ATG AAA TAC CTA TTG CCT ACG GCA GCC GCT GGA TTG TTA TTA
               M   K   Y   L   L   P   T   A   A   A   G   L   L   L
              |_____ PelB Leader Sequence _____

CTC GCT GCC CAA CCA GCG ATG GCG CAC CAT CAT CAC CAT CAC GAT ATC CAG ATG
 L   A   A   Q   P   A   M   A   H   H   H   H   H   H   D   I   Q   M
_____|  |---------6xHis--------| |------ V_L Start ACC CAG TCC CCG TCC TCC CTG AGT GCT TCT GTT GGT GAC CGT GTT ACC ATC ACC
 T   Q   S   P   S   S   L   S   A   S   V   G   D   R   V   T   I   T TGC CGT TCC ACC AAA TCC CTC CTG CAC TCC AAC GGT ATC ACC TAC CTT TAT TGG
 C   R   S   T   K   S   L   L   H   S   N   G   I   T   Y   L   Y   W
     |_____ CDR 1 _____|

TAT CAA CAG AAA CCG GGT AAA GCT CCG AAA CTT CTG ATC TAC CAG ATG TCC AAC
 Y   Q   Q   K   P   G   K   A   P   K   L   L   I   Y   Q   M   S   N
                                                         |_____ CDR 2

CTG GCT TCC GGT GTT CCG TCT CGT TTC TCC AGT TCT GGT TCT GGT ACC GAC TTC
 L   A   S   G   V   P   S   R   F   S   S   S   G   S   G   T   D   F
_____|

ACC CTG ACC ATC TCT TCT CTG CAG CCG GAA GAC TTC GCT ACC TAC TAC TGC GCT
 T   L   T   I   S   S   L   Q   P   E   D   F   A   T   Y   Y   C   A
                                                                     |—

CAG AAC CTG GAA ATC CCG CGT ACC TTC GGT CAG GGT ACC AAA GTT GAA CTT AAG
 Q   N   L   E   I   P   R   T   F   G   Q   G   T   K   V   E   L   K
_____ CDR 3 _____|                                    V_L End

CGC GCT ACC CCG TCT CAC AAC TCC CAC CAG GTT CCA TCC GCA GGC GGT CCG ACT
 R   A   T   P   S   H   N   S   H   Q   V   P   S   A   G   G   P   T
------| |-------------------------------------------- Linker 1 ---------

GCT AAC TCT GGA ACT AGT GGA TCC GAA GTA CAG CTG GTT CAG TCC GGC CCG GGT
 A   N   S   G   T   S   G   S   E   V   Q   L   V   Q   S   G   P   G
-----------------------------------| |---- V_H Start CTT GTT CAA CCG GGT GGT TCC GTT CGT ATC TCT TGC GCT GCT TCT GGT TAC ACG
 L   V   Q   P   G   G   S   V   R   I   S   C   A   A   S   G   Y   T TTC ACC AAC TAC GGC ATG AAC TGG GTC AAA CAG GCT CCG GGT AAA GGC CTG GAA
 F   T   N   Y   G   M   N   W   V   K   Q   A   P   G   K   G   L   E
         |_____ CDR 1 _____|

TGG ATG GGC TGG ATC AAC ACC TAC ACC GGT GAA TCC ACC TAC GCT GAC TCC TTC
 W   M   G   W   I   N   T   Y   T   G   E   S   T   Y   A   D   S   F
             |_____ CDR 2 _____
```

Figure 1 (Continued)

```
AAA GGT CGC TTC ACT TTC TCC CTC GAC ACA AGT GCT AGT GCT GCA TAC CTC CAA
 K   G   R   F   T   F   S   L   D   T   S   A   S   A   A   Y   L   Q

ATC AAC TCG CTG CGT GCA GAG GAT ACA GCA GTC TAT TAC TGC GCC CGT TTC GCT
 I   N   S   L   R   A   E   D   T   A   V   Y   Y   C   A   R   F   A

ATC AAA GGT GAC TAC TGG GGT CAA GGC ACG CTG CTG ACC GTT TCC TCG GAA TTT
 I   K   G   D   Y   W   G   Q   G   T   L   L   T   V   S   S   E   F
 CDR3                                             V_H End

GGT GGC GCG CCG GAG TTC CCG AAA CCG TCC ACC CCG CCG GGT TCT TCT GGT TTA
 G   G   A   P   E   F   P   K   P   S   T   P   P   G   S   S   G   L
 ------------------------------ Linker 2 ------------------------------

GAG GGC GGC AGC CTG GCC GCG CTG ACC GCG CAC CAG GCC TGC CAC CTG CCG CTG
 E   G   G   S   L   A   A   L   T   A   H   Q   A   C   H   L   P   L
 |-- ETA 252-608

GAG ACT TTC ACC CGT CAT CGC CAG CCG CGC GGC TGG GAA CAA CTG GAG CAG TGC
 E   T   F   T   R   H   R   Q   P   R   G   W   E   Q   L   E   Q   C

GGC TAT CCG GTG CAG CGG CTG GTC GCC CTC TAC CTG GCG GCG CGA CTG TCA TGG
 G   Y   P   V   Q   R   L   V   A   L   Y   L   A   A   R   L   S   W

AAC CAG GTC GAC CAG GTG ATC CGC AAC GCC CTG GCC AGC CCC GGC AGC GGC GGC
 N   Q   V   D   Q   V   I   R   N   A   L   A   S   P   G   S   G   G

GAC CTG GGC GAA GCG ATC CGC GAG CAG CCG GAG CAG GCC CGT CTG GCC CTG ACC
 D   L   G   E   A   I   R   E   Q   P   E   Q   A   R   L   A   L   T

CTG GCC GCC GCC GAG AGC GAG CGC TTC GTC CGG CAG GGC ACC GGC AAC GAC GAG
 L   A   A   A   E   S   E   R   F   V   R   Q   G   T   G   N   D   E

GCC GGC GCG GCC AGC GCC GAC GTG GTG AGC CTG ACC TGC CCG GTC GCC GCC GGT
 A   G   A   A   S   A   D   V   V   S   L   T   C   P   V   A   A   G

GAA TGC GCG GGC CCG GCG GAC AGC GGC GAC GCC CTG CTG GAG CGC AAC TAT CCC
 E   C   A   G   P   A   D   S   G   D   A   L   L   E   R   N   Y   P

ACT GGC GCG GAG TTC CTC GGC GAC GGT GGC GAC GTC AGC TTC AGC ACC CGC GGC
 T   G   A   E   F   L   G   D   G   G   D   V   S   F   S   T   R   G

ACG CAG AAC TGG ACG GTG GAG CGG CTG CTC CAG GCG CAC CGC CAA CTG GAG GAG
 T   Q   N   W   T   V   E   R   L   L   Q   A   H   R   Q   L   E   E

CGC GGC TAT GTG TTC GTC GGC TAC CAC GGC ACC TTC CTC GAA GCG GCG CAA AGC
 R   G   Y   V   F   V   G   Y   H   G   T   F   L   E   A   A   Q   S

ATC GTC TTC GGC GGG GTG CGC GCG CGC AGC CAG GAT CTC GAC GCG ATC TGG CGC
 I   V   F   G   G   V   R   A   R   S   Q   D   L   D   A   I   W   R

GGT TTC TAT ATC GCC GGC GAT CCG GCG CTG GCC TAC GGC TAC GCC CAG GAC CAG
 G   F   Y   I   A   G   D   P   A   L   A   Y   G   Y   A   Q   D   Q
```

Figure 1 (Continued)

```
GAA CCC GAC GCG CGC GGC CGG ATC CGC AAC GGT GCC CTG CTG CGG GTC TAT GTG
 E   P   D   A   R   G   R   I   R   N   G   A   L   L   R   V   Y   V

CCG CGC TCC AGC CTG CCG GGC TTC TAC CGC ACC GGC CTG ACC CTG GCC GCG CCG
 P   R   S   S   L   P   G   F   Y   R   T   G   L   T   L   A   A   P

GAG GCG GCG GGC GAG GTC GAA CGG CTG ATC GGC CAT CCG CTG CCG CTG CGC CTG
 E   A   A   G   E   V   E   R   L   I   G   H   P   L   P   L   R   L

GAC GCC ATC ACC GGC CCC GAG GAG GAA GGC GGG CGC CTG GAG ACC ATT CTC GGC
 D   A   I   T   G   P   E   E   E   G   G   R   L   E   T   I   L   G

TGG CCG CTG GCC GAG CGC ACC GTG GTG ATT CCC TCG GCG ATC CCC ACC GAC CCG
 W   P   L   A   E   R   T   V   V   I   P   S   A   I   P   T   D   P

CGC AAC GTC GGT GGC GAC CTC GAC CCG TCC AGC ATC CCC GAC AAG GAA CAG GCG
 R   N   V   G   G   D   L   D   P   S   S   I   P   D   K   E   Q   A

ATC AGC GCC CTG CCG GAC TAC GCC AGC CAG CCC GGC AAA CCG CCG CAT CAC CAC
 I   S   A   L   P   D   Y   A   S   Q   P   G   K   P   P   H   H   H
                                                         |---- 6xHis

CAT CAC CAT AAA GAC GAA CTG TAG TGA CTC GAG  (SEQ ID NO:1)
 H   H   H   K   D   E   L                   (SEQ ID NO:2)
------------|
```

Figure 2: Optimized VB4-845 Nucleotide and Amino Acid Sequences (SEQ ID NOS: 3 and 4)

```
GAA TTC CTG CAG GTC TAT GGA ACG ATA AAT GCC CAT GAA AAT TCT ATT TCA AGG
                                                                    RBS Site AGA CAG TCA TA ATG AAA TAT CTG CTG CCG ACT GCT GCT GCG GGT CTG CTG CTG
               M   K   Y   L   L   P   T   A   A   A   G   L   L   L
               |_____ PelB Leader Sequence _____

CTC GCG GCT CAG CCT GCT ATG GCA CAC CAC CAT CAC CAC CAT GAC ATC CAG ATG
 L   A   A   Q   P   A   M   A   H   H   H   H   H   H   D   I   Q   M
_____| |------  6xHis  ------| |------ V_L Start ACC CAG TCT CCT AGC TCT CTT AGC GCA AGC GTA GGT GAC CGT GTG ACC ATC ACC
 T   Q   S   P   S   S   L   S   A   S   V   G   D   R   V   T   I   T TGC CGT AGC ACT AAA TCT CTG CTG CAT AGC AAC GGC ATC ACC TAC CTG TAT TGG
 C   R   S   T   K   S   L   L   H   S   N   G   I   T   Y   L   Y   W
     |————————————————————— CDR 1 —————————————————————|

TAC CAG CAG AAA CCG GGT AAA GCT CCG AAA CTG CTG ATC TAC CAG ATG TCT AAC
 Y   Q   Q   K   P   G   K   A   P   K   L   L   I   Y   Q   M   S   N
                                                         |____ CDR 2

CTG GCT AGC GGT GTT CCT AGC CGT TTT AGC TCT AGC GGT AGC GGT ACT GAC TTC
 L   A   S   G   V   P   S   R   F   S   S   S   G   S   G   T   D   F
——————————|

ACC CTG ACC ATT AGC TCT CTG CAG CCT GAA GAC TTC GCG ACC TAC TAC TGC GCC
 T   L   T   I   S   S   L   Q   P   E   D   F   A   T   Y   Y   C   A
                                                                     |—

CAG AAC CTT GAA ATC CCG CGT ACT TTC GGC CAG GGT ACC AAA GTC GAA CTG AAA
 Q   N   L   E   I   P   R   T   F   G   Q   G   T   K   V   E   L   K
————————— CDR 3 —————————————|                              V_L End ----

CGT GCG ACC CCG AGC CAT AAC TCT CAC CAG GTT CCT AGC GCA GGT GGT CCG ACT
 R   A   T   P   S   H   N   S   H   Q   V   P   S   A   G   G   P   T
--| |--------------------------------------------------- Linker 1 ----------

GCT AAC TCT GGC ACT AGC GGT TCT GAA GTT CAG CTC GTT CAG TCT GGT CCG GGT
 A   N   S   G   T   S   G   S   E   V   Q   L   V   Q   S   G   P   G
-------------------------------| |---------- V_H Start CTG GTT CAG CCG GGT GGT AGC GTT CGT ATC TCT TGC GCG GCT TCT GGT TAC ACC
 L   V   Q   P   G   G   S   V   R   I   S   C   A   A   S   G   Y   T TTC ACT AAC TAC GGT ATG AAC TGG GTT AAA CAG GCT CCG GGT AAA GGT CTG GAG
 F   T   N   Y   G   M   N   W   V   K   Q   A   P   G   K   G   L   E
         |———— CDR 1 ————|

TGG ATG GGT TGG ATT AAC ACC TAC ACG GGT GAA TCT ACC TAC GCC GAT AGC TTC
 W   M   G   W   I   N   T   Y   T   G   E   S   T   Y   A   D   S   F
             |————————————————————— CDR 2 —————————————————————
```

Figure 2 (Continued)

```
AAA GGT CGT TTC ACC TTT AGC CTT GAC ACC TCT GCG TCT GCG GCG TAC CTT CAG
 K   G   R   F   T   F   S   L   D   T   S   A   S   A   A   Y   L   Q

ATC AAC TCT CTG CGT GCT GAG GAC ACC GCT GTT TAC TAC TGC GCT CGT TTC GCG
 I   N   S   L   R   A   E   D   T   A   V   Y   Y   C   A   R   F   A

ATT AAA GGT GAC TAT TGG GGC CAG GGC ACC CTG CTG ACC GTT AGC TCT GAG TTC
 I   K   G   D   Y   W   G   Q   G   T   L   L   T   V   S   S   E   F
 CDR3                                               V_H End --------||-------

GGT GGT GCG CCT GAG TTC CCT AAA CCG TCT ACC CCG CCA GGT TCT TCT GGT CTT
 G   G   A   P   E   F   P   K   P   S   T   P   P   G   S   S   G   L
-------------------------- Linker 2 ---------------------------------|

GAA GGT GGT AGC TTG GCA GCG TTG ACC GCA CAC CAA GCA TGC CAC CTG CCG CTG
 E   G   G   S   L   A   A   L   T   A   H   Q   A   C   H   L   P   L
|----- ETA 252-608

GAG ACC TTC ACC CGT CAC CGT CAG CCG CGT GGT TGG GAA CAG CTG GAG CAG TGC
 E   T   F   T   R   H   R   Q   P   R   G   W   E   Q   L   E   Q   C

GGT TAT CCG GTT CAG CGT CTG GTA GCT CTG TAC CTG GCT GCT CGT CTG AGC TGG
 G   Y   P   V   Q   R   L   V   A   L   Y   L   A   A   R   L   S   W

AAC CAG GTT GAC CAG GTG ATC CGT AAC GCG CTC GCT AGC CCG GGT TCT GGT GGT
 N   Q   V   D   Q   V   I   R   N   A   L   A   S   P   G   S   G   G

GAC CTG GGT GAA GCT ATC CGT GAA CAG CCG GAA CAA GCT CGT CTC GCG TTG ACC
 D   L   G   E   A   I   R   E   Q   P   E   Q   A   R   L   A   L   T

CTT GCT GCA CCG GAA TCT GAA CGT TTC GTT CGT CAG GGT ACC GGT AAC GAT GAA
 L   A   A   P   E   S   E   R   F   V   R   Q   G   T   G   N   D   E

GCT GGT GCA GCG TCT GCG GAT GTA GTT AGC CTG ACT TGC CCG GTT GCG GCT GGT
 A   G   A   A   S   A   D   V   V   S   L   T   C   P   V   A   A   G

GAA TGC GCT GGT CCG GCA GAC TCT GGT GAC GCG TTG CTT GAA CGT AAC TAC CCG
 E   C   A   G   P   A   D   S   G   D   A   L   L   E   R   N   Y   P

ACC GGT GCT GAG TTC CTG GGT GAC GGT GGT GAC GTT AGC TTT AGC ACC CGT GGT
 T   G   A   E   F   L   G   D   G   G   D   V   S   F   S   T   R   G

ACC CAG AAC TGG ACC GTT GAA CGT CTG CTG CAG GCT CAC CGT CAG CTT GAA GAA
 T   Q   N   W   T   V   E   R   L   L   Q   A   H   R   Q   L   E   E

CGT GGT TAT GTT TTC GTA GGT TAC CAC GGT ACC TTC CTG GAG GCG GCG CAG TCT
 R   G   Y   V   F   V   G   Y   H   G   T   F   L   E   A   A   Q   S

ATC GTG TTC GGT GGT GTT CGT GCT CGT TCC CAG GAC CTT GAC GCA ATT TGG CGC
 I   V   F   G   G   V   R   A   R   S   Q   D   L   D   A   I   W   R

GGT TTC TAC ATC GCG GGT GAC CCA GCG CTC GCG TAC GGT TAC GCT CAG GAC CAG
 G   F   Y   I   A   G   D   P   A   L   A   Y   G   Y   A   Q   D   Q
```

Figure 2 (Continued)

```
GAA CCG GAT GCG CGT GGT CGT ATT CGT AAC GGT GCA CTG CTG CGT GTG TAC GTT
 E   P   D   A   R   G   R   I   R   N   G   A   L   L   R   V   Y   V

CCT CGT TCT AGC CTG CCG GGT TTC TAT CGT ACC GGT CTG ACC CTG GCT GCC CCG
 P   R   S   S   L   P   G   F   Y   R   T   G   L   T   L   A   A   P

GAA GCC GCG GGT GAA GTT GAA CGT CTG ATC GGT CAC CCT CTG CCG CTG CGT CTG
 E   A   A   G   E   V   E   R   L   I   G   H   P   L   P   L   R   L

GAT GCG ATC ACC GGT CCG GAA GAA GAA GGT GGT CGT CTT GAA ACC ATC CTG GGT
 D   A   I   T   G   P   E   E   E   G   G   R   L   E   T   I   L   G

TGG CCG TTG GCT GAG CGT ACT GTA GTC ATC CCG TCT GCG ATC CCG ACC GAC CCG
 W   P   L   A   E   R   T   V   V   I   P   S   A   I   P   T   D   P

CGT AAC GTA GGT GGT GAC CTT GAC CCG TCT AGC ATC CCG GAT AAA GAA CAG GCC
 R   N   V   G   G   D   L   D   P   S   S   I   P   D   K   E   Q   A

ATC AGC GCA CTG CCG GAC TAC GCG TCT CAA CCG GGT AAA CCG CCG CAC CAC CAT
 I   S   A   L   P   D   Y   A   S   Q   P   G   K   P   P   H   H   H
                                                             |--- 6xHis

CAT CAC CAC AAA GAT GAA CTG TAG TGA CTC GAG  (SEQ ID NO:3)
 H   H   H   K   D   E   L   (SEQ ID NO:4)
------------|
```

Figure 3: Optimized VB4-845 Light Chain Nucleotide and Amino Acid Sequences
(SEQ ID NOS: 5 and 6)

```
GAC ATC CAG ATG ACC CAG TCT CCT AGC TCT CTT AGC GCA AGC GTA GGT GAC CGT
 D   I   Q   M   T   Q   S   P   S   S   L   S   A   S   V   G   D   R
|------ V_L Start GTG ACC ATC ACC TGC CGT AGC ACT AAA TCT CTG CTG CAT AGC AAC GGC ATC ACC
 V   T   I   T   C   R   S   T   K   S   L   L   H   S   N   G   I   T
                     |                 CDR 1

TAC CTG TAT TGG TAC CAG CAG AAA CCG GGT AAA GCT CCG AAA CTG CTG ATC TAC
 Y   L   Y   W   Y   Q   Q   K   P   G   K   A   P   K   L   L   I   Y
             |

CAG ATG TCT AAC CTG GCT AGC GGT GTT CCT AGC CGT TTT AGC TCT AGC GGT AGC
 Q   M   S   N   L   A   S   G   V   P   S   R   F   S   S   S   G   S
 |         CDR 2         |

GGT ACT GAC TTC ACC CTG ACC ATT AGC TCT CTG CAG CCT GAA GAC TTC GCG ACC
 G   T   D   F   T   L   T   I   S   S   L   Q   P   E   D   F   A   T

TAC TAC TGC GCC CAG AAC CTT GAA ATC CCG CGT ACT TTC GGC CAG GGT ACC AAA
 Y   Y   C   A   Q   N   L   E   I   P   R   T   F   G   Q   G   T   K
             |            CDR 3            |

GTC GAA CTG AAA CGT (SEQ ID NO:5)
 V   E   L   K   R  (SEQ ID NO:6)
        V_L End ----
```

Figure 4: Optimized VB4-845 Heavy Chain Nucleotide and Amino Acid Sequences
(SEQ ID NOS:7 and 8)

```
GAA GTT CAG CTC GTT CAG TCT GGT CCG GGT CTG GTT CAG CCG GGT GGT AGC GTT
 E   V   Q   L   V   Q   S   G   P   G   L   V   Q   P   G   G   S   V
|--- V_H Start CGT ATC TCT TGC GCG GCT TCT GGT TAC ACC TTC ACT AAC TAC GGT ATG AAC TGG
 R   I   S   C   A   A   S   G   Y   T   F   T   N   Y   G   M   N   W
                                             |———— CDR 1 ————|

GTT AAA CAG GCT CCG GGT AAA GGT CTG GAG TGG ATG GGT TGG ATT AAC ACC TAC
 V   K   Q   A   P   G   K   G   L   E   W   M   G   W   I   N   T   Y
                                                 |————————— CDR 2

ACG GGT GAA TCT ACC TAC GCC GAT AGC TTC AAA GGT CGT TTC ACC TTT AGC CTT
 T   G   E   S   T   Y   A   D   S   F   K   G   R   F   T   F   S   L
 ——————————————————————————————————————————|

GAC ACC TCT GCG TCT GCG GCG TAC CTT CAG ATC AAC TCT CTG CGT GCT GAG GAC
 D   T   S   A   S   A   A   Y   L   Q   I   N   S   L   R   A   E   D

ACC GCT GTT TAC TAC TGC GCT CGT TTC GCG ATT AAA GGT GAC TAT TGG GGC CAG
 T   A   V   Y   Y   C   A   R   F   A   I   K   G   D   Y   W   G   Q
                             |————————— CDR3 —————————|

GGC ACC CTG CTG ACC GTT AGC TCT (SEQ ID NO:7)
 G   T   L   L   T   V   S   S  (SEQ ID NO:8)
              V_H End --------|
```

Figure 5: Optimized Exotoxin A Nucleotide and Amino Acid Sequences (SEQ ID NOS: 9 and 10)

```
GAA GGT GGT AGC TTG GCA GCG TTG ACC GCA CAC CAA GCA TGC CAC CTG CCG CTG
 E   G   G   S   L   A   A   L   T   A   H   Q   A   C   H   L   P   L
|----- ETA 252-608

GAG ACC TTC ACC CGT CAC CGT CAG CCG CGT GGT TGG GAA CAG CTG GAG CAG TGC
 E   T   F   T   R   H   R   Q   P   R   G   W   E   Q   L   E   Q   C

GGT TAT CCG GTT CAG CGT CTG GTA GCT CTG TAC CTG GCT GCT CGT CTG AGC TGG
 G   Y   P   V   Q   R   L   V   A   L   Y   L   A   A   R   L   S   W

AAC CAG GTT GAC CAG GTG ATC CGT AAC GCG CTC GCT AGC CCG GGT TCT GGT GGT
 N   Q   V   D   Q   V   I   R   N   A   L   A   S   P   G   S   G   G

GAC CTG GGT GAA GCT ATC CGT GAA CAG CCG GAA CAA GCT CGT CTC GCG TTG ACC
 D   L   G   E   A   I   R   E   Q   P   E   Q   A   R   L   A   L   T

CTT GCT GCA GCG GAA TCT GAA CGT TTC GTT CGT CAG GGT ACC GGT AAC GAT GAA
 L   A   A   A   E   S   E   R   F   V   R   Q   G   T   G   N   D   E

GCT GGT GCA GCG TCT GCG GAT GTA GTT AGC CTG ACT TGC CCG GTT GCG GCT GGT
 A   G   A   A   S   A   D   V   V   S   L   T   C   P   V   A   A   G

GAA TGC GCT GGT CCG GCA GAC TCT GGT GAC GCG TTG CTT GAA CGT AAC TAC CCG
 E   C   A   G   P   A   D   S   G   D   A   L   L   E   R   N   Y   P

ACC GGT GCT GAG TTC CTG GGT GAC GGT GGT GAC GTT AGC TTT AGC ACC CGT GGT
 T   G   A   E   F   L   G   D   G   G   D   V   S   F   S   T   R   G

ACC CAG AAC TGG ACC GTT GAA CGT CTG CTG CAG GCT CAC CGT CAG CTT GAA GAA
 T   Q   N   W   T   V   E   R   L   L   Q   A   H   R   Q   L   E   E

CGT GGT TAT GTT TTC GTA GGT TAC CAC GGT ACC TTC CTG GAG GCG GCG CAG TCT
 R   G   Y   V   F   V   G   Y   H   G   T   F   L   E   A   A   Q   S

ATC GTG TTC GGT GGT GTT CGT GCT CGT TCC CAG GAC CTT GAC GCA ATT TGG CGC
 I   V   F   G   G   V   R   A   R   S   Q   D   L   D   A   I   W   R

GGT TTC TAC ATC GCG GGT GAC CCA GCG CTC GCG TAC GGT TAC GCT CAG GAC CAG
 G   F   Y   I   A   G   D   P   A   L   A   Y   G   Y   A   Q   D   Q

GAA CCG GAT GCG CGT GGT CGT ATT CGT AAC GGT GCA CTG CTG CGT GTG TAC GTT
 E   P   D   A   R   G   R   I   R   N   G   A   L   L   R   V   Y   V

CCT CGT TCT AGC CTG CCG GGT TTC TAT CGT ACC GGT CTG ACC CTG GCT GCC CCG
 P   R   S   S   L   P   G   F   Y   R   T   G   L   T   L   A   A   P

GAA GCC GCG GGT GAA GTT GAA CGT CTG ATC GGT CAC CCT CTG CCG CTG CGT CTG
 E   A   A   G   E   V   E   R   L   I   G   H   P   L   P   L   R   L

GAT GCG ATC ACC GGT CCG GAA GAA GAA GGT GGT CGT CTT GAA ACC ATC CTG GGT
 D   A   I   T   G   P   E   E   E   G   G   R   L   E   T   I   L   G

TGC CCG TTG GCT GAG CGT ACT GTA GTC ATC CCG TCT GCG ATC CCG ACC GAC CCG
 W   P   L   A   E   R   T   V   V   I   P   S   A   I   P   T   D   P
```

Figure 5(Continued)

```
CGT AAC GTA GGT GGT GAC CTT GAC CCG TCT AGC ATC CCG GAT AAA GAA CAG GCC
 R   N   V   G   G   D   L   D   P   S   S   I   P   D   K   E   Q   A

ATC AGC GCA CTG CCG GAC TAC GCG TCT CAA CCG GGT AAA CCG CCG (SEQ ID NO:9)
 I   S   A   L   P   D   Y   A   S   Q   P   G   K   P   P  (SEQ ID NO:10)
```

Figure 6: Optimized VB4-845 Nucleotide and Amino Acid Sequences for RBS, Leaders, Histidines and Linkers (SEQ ID NOS: 11 to 21)

Sequence with RBS site (SEQ ID 11)

GAA TTC CTG CAG GTC TAT GGA ACG ATA AAT GCC CAT GAA AAT TCT ATT TCA AGG
                                                                    RBS Site
AGA CAG TCA TA

Optimized PelB Leader Sequence

ATG AAA TAT CTG CTG CCG ACT GCT GCT GCG GGT CTG CTG CTG CTC GCG GCT CAG
 M   K   Y   L   L   P   T   A   A   A   G   L   L   L   L   A   A   Q

CCT GCT ATG GCA (SEQ ID NO:12)
 P   A   M   A  (SEQ ID NO:13)

Optimized Histidine Sequence

CAC CAC CAT CAC CAC CAT (SEQ ID NO:14)
 H   H   H   H   H   H  (SEQ ID NO:15)

Optimized Linker 1 Sequence

GCG ACC CCG AGC CAT AAC TCT CAC CAG GTT CCT AGC GCA GGT GGT CCG ACT
 A   T   P   S   H   N   S   H   Q   V   P   S   A   G   G   P   T

GCT AAC TCT GGC ACT AGC GGT TCT (SEQ ID NO:16)
 A   N   S   G   T   S   G   S  (SEQ ID NO:17)

Optimized Linker 2 Sequence

GAG TTC GGT GGT GCG CCT GAG TTC CCT AAA CCG TCT ACC CCG CCA GGT TCT TCT
 E   F   G   G   A   P   E   F   P   K   P   S   T   P   P   G   S   S

GGT CTT (SEQ ID NO:18)
 G   L  (SEQ ID NO:19)

Optimized Second Histidine Sequence with KDEL

CAC CAC CAT CAT CAC CAC AAA GAT GAA CTG TAG TGA CTC GAG (SEQ ID NO:20)
CAC CAC CAT CAT CAC CAC AAA GAT GAA CTG (SEQ ID NO:30)
 H   H   H   H   H   H   K   D   E   L  (SEQ ID NO:21)

Figure 7:Comparison of VB4-845 Original (Or) and Optimized (Op) Sequences
Nucleotide Changes are Shown in Bold and Underlined in the Original
Sequence (SEQ ID NOS: 22 to 29)

RBS Optimized/ RBS Original
(Op)GAA TTC CTG CAG GTC TAT GGA ACG ATA AAT GCC CAT GAA AAT TCT ATT TCA AGG
(Or)GAA TTC CTG CAG GTC TAT GGA ACG ATA AAT GCC CAT GAA AAT TCT ATT TCA AGG (Op)AGA CAG TCA TA (SEQ ID NO:11)
(Or)AGA CAG TCA TA (SEQ ID NO:11)

PelB Leader Optimized/ PelB Leader Original
(Op)ATG AAA TAT CTG CTG CCG ACT GCT GCT GCG GGT CTG CTG CTG CTC GCG GCT CAG
(Or)ATG AAA TAC CTA TTG CCT ACG GCA GCC GCT GGA TTG TTA TTA CTC GCT GCC CAA (Op)CCT GCT ATG GCA (SEQ ID NO:12)
(Or)CCA GCG ATG GCG (SEQ ID NO:22)

Histidine Optimized/ Histidine Original
(Op)CAC CAC CAT CAC CAC CAT (SEQ ID NO:14)
(Or)CAC CAT CAT CAC CAT CAC (SEQ ID NO:23)

V_L Optimized/ V_L Original
(Op)GAC ATC CAG ATG ACC CAG TCT CCT AGC TCT CTT AGC GCA AGC GTA GGT GAC CGT
(Or)GAT ATC CAG ATG ACC CAG TCC CCG TCC TCC CTG AGT GCT TCT GTT GGT GAC CGT (Op)GTG ACC ATC ACC TGC CGT AGC ACT AAA TCT CTG CTG CAT AGC AAC GGC ATC ACC
(Or)GTT ACC ATC ACC TGC CGT TCC ACC AAA TCC CTC CTG CAC TCC AAC GGT ATC ACC (Op)TAC CTG TAT TGG TAC CAG CAG AAA CCG GGT AAA GCT CCG AAA CTG CTG ATC TAC
(Or)TAC CTT TAT TGG TAT CAA CAG AAA CCG GGT AAA GCT CCG AAA CTT CTG ATC TAC (Op)CAG ATG TCT AAC CTG GCT AGC GGT GTT CCT AGC CGT TTT AGC TCT AGC GGT AGC
(Or)CAG ATG TCC AAC CTG GCT TCC GGT GTT CCG TCT CGT TTC TCC AGT TCT GGT TCT (Op)GGT ACT GAC TTC ACC CTG ACC ATT AGC TCT CTG CAG CCT GAA GAC TTC GCG ACC
(Or)GGT ACC GAC TTC ACC CTG ACC ATC TCT TCT CTG CAG CCG GAA GAC TTC GCT ACC (Op)TAC TAC TGC GCC CAG AAC CTT GAA ATC CGT ACT TTC GGC CAG GGT ACC AAA
(Or)TAC TAC TGC GCT CAG AAC CTG GAA ATC CGT ACC TTC GGT CAG GGT ACC AAA (Op)GTC GAA CTG AAA CGT (SEQ ID NO:5)
(Or)GTT GAA CTT AAG CGC (SEQ ID NO:24)

Linker 1 Optimized/Linker 1 Original (SEQ ID NOS: 16 and 25)
(Op)GCG ACC CCG AGC CAT AAC TCT CAC CAG GTT CCT AGC GCA GGT GGT CCG ACT GCT
(Or)GCT ACC CCG TCT CAC AAC TCC CAC CAG GTT CCA TCC GCA GGC GGT CCG ACT GCT (Op)AAC TCT GGC ACT AGC GGT TCT (SEQ ID NO:16)
(Or)AAC TCT GGA ACT AGT GGA TCC (SEQ ID NO:25)

Figure 7 (Continued)

V_H Optimized/ V_H Original
(Op)GAA GTT CAG CTC GTT CAG TCT GGT CCG GGT CTG GTT CAG CCG GGT GGT AGC GTT
(Or)GAA GTA CAG CTG GTT CAG TCC GGC CCG GGT CTT GTT CAA CCG GGT GGT TCC GTT (Op)CGT ATC TCT TGC GCG GCT TCT GGT TAC ACC TTC ACT AAC TAC GGT ATG AAC TGG
(Or)CGT ATC TCT TGC GCT GCT TCT GGT TAC ACG TTC ACC AAC TAC GGC ATG AAC TGG (Op)GTT AAA CAG GCT CCG GGT AAA GGT CTG GAG TGG ATG GGT TGG ATT AAC ACC TAC
(Or)GTC AAA CAG GCT CCG GGT AAA GGC CTG GAA TGG ATG GGC TGG ATC AAC ACC TAC (Op)ACG GGT GAA TCT ACC TAC GCC GAT AGC TTC AAA GGT CGT TTC ACC TTT AGC CTT
(Or)ACC GGT GAA TCC ACC TAC GCT GAC TCC TTC AAA GGT CGC TTC ACT TTC TCC CTC (Op)GAC ACC TCT GCG TCT GCG GCG TAC CTT CAG ATC AAC TCT CTG CGT GCT GAG GAC
(Or)GAC ACA AGT GCT AGT GCT GCA TAC CTC CAA ATC AAC TCG CTG CGT GCA GAG GAT (Op)ACC GCT GTT TAC TAC TGC GCT CGT TTC GCG ATT AAA GGT GAC TAT TGG GGC CAG
(Or)ACA GCA GTC TAT TAC TGC GCC CGT TTC GCT ATC AAA GGT GAC TAC TGG GGT CAA (Op)GGC ACC CTG CTG ACC GTT AGC TCT (SEQ ID NO:7)
(Or)GGC ACG CTG CTG ACC GTT TCC TCG (SEQ ID NO:26)

Linker 2 Optimized/Linker 2 Original
(Op)GAG TTC GGT GGT GCG CCT GAG TTC CCT AAA CCG TCT ACC CCG CCA GGT TCT TCT
(Or)GAA TTT GGT GGC GCG CCG GAG TTC CCG AAA CCG TCC ACC CCG CCG GGT TCT TCT (Op)GGT CTT (SEQ ID NO:18)
(Or)GGT TTA (SEQ ID NO:27)

ETA_252-608 Optimized/ ETA_252-608 Original
(Op)GAA GGT GGT AGC TTG GCA GCG TTG ACC GCA CAC CAA GCA TGC CAC CTG CCG CTG
(Or)GAG GGC GGC AGC CTG GCC GCG CTG ACC GCG CAC CAG GCC TGC CAC CTG CCG CTG (Op)GAG ACC TTC ACC CGT CAC CGT CAG CCG CGT GGT TGG GAA CAG CTG GAG CAG TGC
(Or)GAG ACT TTC ACC CGT CAT CGC CAG CCG CGC GGC TGG GAA CAA CTG GAG CAG TGC (Op)GGT TAT CCG GTT CAG CGT CTG GTA GCT CTG TAC CTG GCT GCT CGT CTG AGC TGG
(Or)GGC TAT CCG GTG CAG CGG CTG GTC GCC CTC TAC CTG GCG GCG CGA CTG TCA TGG (Op)AAC CAG GTT GAC CAG GTG ATC CGT AAC GCG CTC GCT AGC CCG GGT TCT GGT GGT
(Or)AAC CAG GTC GAC CAG GTG ATC CGC AAC GCC CTG GCC AGC CCC GGC AGC GGC GGC (Op)GAC CTG GGT GAA GCT ATC CGT GAA CAG CCG GAA CAA GCT CGT CTC GCG TTG ACC
(Or)GAC CTG GGC GAA GCG ATC CGC GAG CAG CCG GAG CAG GCC CGT CTG GCC CTG ACC (Op)CTT GCT GCA GCG GAA TCT GAA CGT TTC GTT CGT CAG GGT ACC GGT AAC GAT GAA
(Or)CTG GCC GCC GCC GAG AGC GAG CGC TTC GTC CGG CAG GGC ACC GGC AAC GAC GAG (Op)GCT GGT GCA GCG TCT GCG GAT GTA GTT AGC CTG ACT TGC CCG GTT GCG GCT GGT
(Or)GCC GGC GCG GCC AGC GCC GAC GTG GTG AGC CTG ACC TGC CCG GTC GCC GCC GGT (Op)GAA TGC GCT GGT CCG GCA GAC TCT GGT GAC GCG TTG CTT GAA CGT AAC TAC CCG
(Or)GAA TGC GCG GGC CCG GCG GAC AGC GGC GAC GCC CTG CTG GAG CGC AAC TAT CCC (Op)ACC GGT GCT GAG TTC CTG GGT GAC GGT GGT GAC GTT AGC TTT AGC ACC CGT GGT
(Or)ACT GGC GCG GAG TTC CTC GGC GAC GGT GGC GAC GTC AGC TTC AGC ACC CGC GGC

Figure 7 (Continued)

```
(Op)ACC CAG AAC TGG ACC GTT GAA CGT CTG CTG CAG GCT CAC CGT CAG CTT GAA GAA
(Or)ACG CAG AAC TGG ACG GTG GAG CGG CTG CTC CAG GCG CAC CGC CAA CTG GAG GAG (Op)CGT GGT TAT GTT TTC GTA GGT TAC CAC GGT ACC TTC CTG GAG GCG GCG CAG TCT
(Or)CGC GGC TAT GTG TTC GTC GGC TAC CAC GGC ACC TTC CTC GAA GCG GCG CAA AGC (Op)ATC GTG TTC GGT GGT GTT CGT GCT CGT TCC CAG GAC CTT GAC GCA ATT TGG CGC
(Or)ATC GTC TTC GGC GGG GTG CGC GCG CGC AGC CAG GAT CTC GAC GCG ATC TGG CGC (Op)GGT TTC TAC ATC GCG GGT GAC CCA GCG CTC GCG TAC GGT TAC GCT CAG GAC CAG
(Or)GGT TTC TAT ATC GCC GGC GAT CCG GCG CTG GCC TAC GGC TAC GCC CAG GAC CAG (Op)GAA CCG GAT GCG CGT GGT CGT ATT CGT AAC GGT GCA CTG CTG CGT GTG TAC GTT
(Or)GAA CCC GAC GCG CGC GGC CGG ATC CGC AAC GGT GCC CTG CTG CGG GTC TAT GTG (Op)CCT CGT TCT AGC CTG CCG GGT TTC TAT CGT ACC GGT CTG ACC CTG GCT GCC CCG
(Or)CCG CGC TCC AGC CTG CCG GGC TTC TAC CGC ACC GGC CTG ACC CTG GCC GCG CCG (Op)GAA GCC GCG GGT GAA GTT GAA CGT CTG ATC GGT CAC CCT CTG CCG CTG CGT CTG
(Or)GAG GCG GCG GGC GAG GTC GAA CGG CTG ATC GGC CAT CCG CTG CCG CTG CGC CTG (Op)GAT GCG ATC ACC GGT CCG GAA GAA GAA GGT GGT CGT CTT GAA ACC ATC CTG GGT
(Or)GAC GCC ATC ACC GGC CCC GAG GAG GAA GGC GGG CGC CTG GAG ACC ATT CTC GGC (Op)TGG CCG TTG GCT GAG CGT ACT GTA GTC ATC CCG TCT GCG ATC CCG ACC GAC CCG
(Or)TGG CCG CTG GCC GAG CGC ACC GTG GTG ATT CCC TCG GCG ATC CCC ACC GAC CCG (Op)CGT AAC GTA GGT GGT GAC CTT GAC CCG TCT AGC ATC CCG GAT AAA GAA CAG GCC
(Or)CGC AAC GTC GGT GGC GAC CTC GAC CCG TCC AGC ATC CCC GAC AAG GAA CAG GCG (Op)ATC AGC GCA CTG CCG GAC TAC GCG TCT CAA CCG GGT AAA CCG CCG (SEQ ID NO:9)
(Or)ATC AGC GCC CTG CCG GAC TAC GCC AGC CAG CCC GGC AAA CCG CCG (SEQ ID NO:28)
```

Final Histidine and KDEL Optimized/ Final Histidine and KDEL Original
```
(Op)CAC CAC CAT CAT CAC CAC AAA GAT GAA CTG TAG TGA CTC GAG (SEQ ID NO:20)
(Op)CAC CAC CAT CAT CAC CAC AAA GAT GAA CTG (SEQ ID NO:30)
(Or)CAT CAC CAC CAT CAC CAT AAA GAC GAA CTG TAG TGA CTC GAG (SEQ ID NO:29)
(Or)CAT CAC CAC CAT CAC CAT AAA GAC GAA CTG (SEQ ID NO:31)
```

Legend

| Lane # | Sample |
|---|---|
| 1 | VB4-845 optimized E104-Xoma |
| 2 | VB4-845 optimized E104-Xoma |
| 3 | VB4-845 optimized E104-Xoma |
| 4 | VB4-845 optimized E104-Xoma |
| 5 | VB4-845 optimized E104-GMM |
| 6 | VB4-845 optimized E104-GMM |
| 7 | VB4-845 optimized E104-GMM |
| 8 | VB4-845 optimized E104-GMM |
| 9 | Marker |
| 10 | Uninduced |
| 11 | VB4-845 original E104-GMM |

SEQUENCE LISTING

```
<160> NUMBER OF SEQ ID NOS: 31

<210> SEQ ID NO 1
<211> LENGTH: 2084
<212> TYPE: DNA
<213> ORGANISM: Artificial Sequence
<220> FEATURE:
<223> OTHER INFORMATION: VB4-845 Nucleotide

<400> SEQUENCE: 1
gaattcctgc aggtctatgg aacgataaat gcccatgaaa attctatttc aaggagacag      60
tcataatgaa atacctattg cctacggcag ccgctggatt gttattactc gctgcccaac     120
cagcgatggc gcaccatcat caccatcacg atatccagat gacccagtcc ccgtcctccc     180
tgagtgcttc tgttggtgac cgtgttacca tcacctgccg ttccaccaaa tccctcctgc     240
actccaacgg tatcacctac ctttattggt atcaacagaa accgggtaaa gctccgaaac     300
ttctgatcta ccagatgtcc aacctggctt ccggtgttcc gtctcgtttc tccagttctg     360
gttctggtac cgacttcacc ctgaccatct cttctctgca gccggaagac ttcgctacct     420
actactgcgc tcagaacctg gaaatcccgc gtaccttcgg tcagggtacc aaagttgaac     480
ttaagcgcgc tacccgtct cacaactccc accaggttcc atccgcaggc ggtccgactg      540
ctaactctgg aactagtgga tccgaagtac agctggttca gtccggcccg ggtcttgttc     600
aaccgggtgg ttccgttcgt atctcttgcg ctgcttctgg ttacacgttc accaactacg     660
gcatgaactg ggtcaaacag gctccgggta aaggcctgga atggatgggc tggatcaaca     720
cctacaccgg tgaatccacc tacgctgact ccttcaaagg tcgcttcact ttctccctcg     780
acacaagtgc tagtgctgca tacctccaaa tcaactcgct gcgtgcagag gatacagcag     840
tctattactg cgcccgtttc gctatcaaag gtgactactg gggtcaaggc acgctgctga     900
ccgtttcctc ggaatttggt ggcgcgccgg agttcccgaa accgtccacc ccgccgggtt     960
cttctggttt agagggcggc agcctggccg cgctgaccgc gcaccaggcc tgccacctgc    1020
cgctggagac tttcacccgt catcgccagc cgcgcggctg ggaacaactg gagcagtgcg    1080
```

-continued

```
gctatccggt gcagcggctg gtcgccctct acctggcggc gcgactgtca tggaaccagg    1140
tcgaccaggt gatccgcaac gccctggcca gccccggcag cggcggcgac ctgggcgaag    1200
cgatccgcga gcagccggag caggcccgtc tggccctgac cctggccgcc gccgagagcg    1260
agcgcttcgt ccggcagggc accggcaacg acgaggccgg cgcggccagc gccgacgtgg    1320
tgagcctgac ctgcccggtc gccgccggtg aatgcgcggg cccggcggac agcggcgacg    1380
ccctgctgga gcgcaactat cccactggcg cggagttcct cggcgacggt ggcgacgtca    1440
gcttcagcac ccgcggcacg cagaactgga cggtggagcg gctgctccag gcgcaccgcc    1500
aactggagga gcgcggctat gtgttcgtcg gctaccacgg caccttcctc gaagcggcgc    1560
aaagcatcgt cttcggcggg gtgcgcgcgc gcagccagga tctcgacgcg atctggcgcg    1620
gtttctatat cgccggcgat ccggcgctgg cctacggcta cgcccaggac caggaacccg    1680
acgcgcgcgg ccggatccgc aacggtgccc tgctgcgggt ctatgtgccg cgctccagcc    1740
tgccgggctt ctaccgcacc ggcctgaccc tggccgcgcc ggaggcggcg ggcgaggtcg    1800
aacggctgat cggccatccg ctgccgctgc gcctggacgc catcaccggc cccgaggagg    1860
aaggcgggcg cctggagacc attctcggct ggccgctggc cgagcgcacc gtggtgattc    1920
cctcggcgat ccccaccgac ccgcgcaacg tcggtggcga cctcgacccg tccagcatcc    1980
ccgacaagga acaggcgatc agcgccctgc cggactacgc cagccagccc ggcaaaccgc    2040
cgcatcacca ccatcaccat aaagacgaac tgtagtgact cgag                    2084
```

<210> SEQ ID NO 2
<211> LENGTH: 669
<212> TYPE: PRT
<213> ORGANISM: Artificial Sequence
<220> FEATURE:
<223> OTHER INFORMATION: PelB VB4-845 amino acid

<400> SEQUENCE: 2

```
Met Lys Tyr Leu Leu Pro Thr Ala Ala Ala Gly Leu Leu Leu Leu Ala
1               5                  10                  15

Ala Gln Pro Ala Met Ala His His His His His His Asp Ile Gln Met
            20                  25                  30

Thr Gln Ser Pro Ser Ser Leu Ser Ala Ser Val Gly Asp Arg Val Thr
        35                  40                  45

Ile Thr Cys Arg Ser Thr Lys Ser Leu Leu His Ser Asn Gly Ile Thr
    50                  55                  60

Tyr Leu Tyr Trp Tyr Gln Gln Lys Pro Gly Lys Ala Pro Lys Leu Leu
65                  70                  75                  80

Ile Tyr Gln Met Ser Asn Leu Ala Ser Gly Val Pro Ser Arg Phe Ser
                85                  90                  95

Ser Ser Gly Ser Gly Thr Asp Phe Thr Leu Thr Ile Ser Ser Leu Gln
            100                 105                 110

Pro Glu Asp Phe Ala Thr Tyr Tyr Cys Ala Gln Asn Leu Glu Ile Pro
        115                 120                 125

Arg Thr Phe Gly Gln Gly Thr Lys Val Glu Leu Lys Arg Ala Thr Pro
    130                 135                 140

Ser His Asn Ser His Gln Val Pro Ser Ala Gly Gly Pro Thr Ala Asn
145                 150                 155                 160

Ser Gly Thr Ser Gly Ser Glu Val Gln Leu Val Gln Ser Gly Pro Gly
                165                 170                 175

Leu Val Gln Pro Gly Gly Ser Val Arg Ile Ser Cys Ala Ala Ser Gly
            180                 185                 190
```

```
Tyr Thr Phe Thr Asn Tyr Gly Met Asn Trp Val Lys Gln Ala Pro Gly
            195                 200                 205

Lys Gly Leu Glu Trp Met Gly Trp Ile Asn Thr Tyr Thr Gly Glu Ser
    210                 215                 220

Thr Tyr Ala Asp Ser Phe Lys Gly Arg Phe Thr Phe Ser Leu Asp Thr
225                 230                 235                 240

Ser Ala Ser Ala Ala Tyr Leu Gln Ile Asn Ser Leu Arg Ala Glu Asp
                245                 250                 255

Thr Ala Val Tyr Tyr Cys Ala Arg Phe Ala Ile Lys Gly Asp Tyr Trp
            260                 265                 270

Gly Gln Gly Thr Leu Leu Thr Val Ser Ser Glu Phe Gly Ala Pro
            275                 280                 285

Glu Phe Pro Lys Pro Ser Thr Pro Pro Gly Ser Ser Gly Leu Glu Gly
    290                 295                 300

Gly Ser Leu Ala Ala Leu Thr Ala His Gln Ala Cys His Leu Pro Leu
305                 310                 315                 320

Glu Thr Phe Thr Arg His Arg Gln Pro Arg Gly Trp Glu Gln Leu Glu
                325                 330                 335

Gln Cys Gly Tyr Pro Val Gln Arg Leu Val Ala Leu Tyr Leu Ala Ala
            340                 345                 350

Arg Leu Ser Trp Asn Gln Val Asp Gln Val Ile Arg Asn Ala Leu Ala
            355                 360                 365

Ser Pro Gly Ser Gly Gly Asp Leu Gly Glu Ala Ile Arg Glu Gln Pro
370                 375                 380

Glu Gln Ala Arg Leu Ala Leu Thr Leu Ala Ala Ala Glu Ser Glu Arg
385                 390                 395                 400

Phe Val Arg Gln Gly Thr Gly Asn Asp Glu Ala Gly Ala Ala Ser Ala
                405                 410                 415

Asp Val Val Ser Leu Thr Cys Pro Val Ala Ala Gly Glu Cys Ala Gly
            420                 425                 430

Pro Ala Asp Ser Gly Asp Ala Leu Leu Glu Arg Asn Tyr Pro Thr Gly
            435                 440                 445

Ala Glu Phe Leu Gly Asp Gly Gly Asp Val Ser Phe Ser Thr Arg Gly
    450                 455                 460

Thr Gln Asn Trp Thr Val Glu Arg Leu Leu Gln Ala His Arg Gln Leu
465                 470                 475                 480

Glu Glu Arg Gly Tyr Val Phe Val Gly Tyr His Gly Thr Phe Leu Glu
                485                 490                 495

Ala Ala Gln Ser Ile Val Phe Gly Gly Val Arg Ala Arg Ser Gln Asp
            500                 505                 510

Leu Asp Ala Ile Trp Arg Gly Phe Tyr Ile Ala Gly Asp Pro Ala Leu
            515                 520                 525

Ala Tyr Gly Tyr Ala Gln Asp Gln Glu Pro Asp Ala Arg Gly Arg Ile
    530                 535                 540

Arg Asn Gly Ala Leu Leu Arg Val Tyr Val Pro Arg Ser Ser Leu Pro
545                 550                 555                 560

Gly Phe Tyr Arg Thr Gly Leu Thr Leu Ala Ala Pro Glu Ala Ala Gly
                565                 570                 575

Glu Val Glu Arg Leu Ile Gly His Pro Leu Pro Leu Arg Leu Asp Ala
            580                 585                 590

Ile Thr Gly Pro Glu Glu Glu Gly Gly Arg Leu Glu Thr Ile Leu Gly
            595                 600                 605

Trp Pro Leu Ala Glu Arg Thr Val Val Ile Pro Ser Ala Ile Pro Thr
610                 615                 620
```

Asp Pro Arg Asn Val Gly Gly Asp Leu Asp Pro Ser Ser Ile Pro Asp
625                 630                 635                 640

Lys Glu Gln Ala Ile Ser Ala Leu Pro Asp Tyr Ala Ser Gln Pro Gly
                645                 650                 655

Lys Pro Pro His His His His His His Lys Asp Glu Leu
            660                 665

<210> SEQ ID NO 3
<211> LENGTH: 2084
<212> TYPE: DNA
<213> ORGANISM: Artificial Sequence
<220> FEATURE:
<223> OTHER INFORMATION: Optimized VB4-845 nucleotide

<400> SEQUENCE: 3

| | | | | | |
|---|---|---|---|---|---|
| gaattcctgc | aggtctatgg | aacgataaat | gcccatgaaa | attctatttc | aaggagacag | 60 |
| tcataatgaa | atatctgctg | ccgactgctg | ctgcgggtct | gctgctgctc | gcggctcagc | 120 |
| ctgctatggc | acaccaccat | caccaccatg | acatccagat | gacccagtct | cctagctctc | 180 |
| ttagcgcaag | cgtaggtgac | cgtgtgacca | tcacctgccg | tagcactaaa | tctctgctgc | 240 |
| atagcaacgg | catcacctac | ctgtattggt | accagcagaa | accgggtaaa | gctccgaaac | 300 |
| tgctgatcta | ccagatgtct | aacctggcta | gcggtgttcc | tagccgtttt | agctctagcg | 360 |
| gtagcggtac | tgacttcacc | ctgaccatta | gctctctgca | gcctgaagac | ttcgcgacct | 420 |
| actactgcgc | ccagaacctt | gaaatcccgc | gtactttcgg | ccagggtacc | aaagtcgaac | 480 |
| tgaaacgtgc | gaccccgagc | cataactctc | accaggttcc | tagcgcaggt | ggtccgactg | 540 |
| ctaactctgg | cactagcggt | tctgaagttc | agctcgttca | gtctggtccg | ggtctggttc | 600 |
| agccgggtgg | tagcgttcgt | atctcttgcg | cggcttctgg | ttacaccttc | actaactacg | 660 |
| gtatgaactg | ggttaaacag | gctccgggta | aaggtctgga | gtggatgggt | tggattaaca | 720 |
| cctacacggg | tgaatctacc | tacgccgata | gcttcaaagg | tcgtttcacc | tttagccttg | 780 |
| acacctctgc | gtctgcggcg | taccttcaga | tcaactctct | gcgtgctgag | gacaccgctg | 840 |
| tttactactg | cgctcgtttc | gcgattaaag | gtgactattg | gggccagggc | accctgctga | 900 |
| ccgttagctc | tgagttcggt | ggtgcgcctg | agttccctaa | accgtctacc | ccgccaggtt | 960 |
| cttctggtct | tgaaggtggt | agcttggcag | cgttgaccgc | acaccaagca | tgccacctgc | 1020 |
| cgctggagac | cttcacccgt | caccgtcagc | cgcgtggttg | ggaacagctg | gagcagtgcg | 1080 |
| gttatccggt | tcagcgtctg | gtagctctgt | acctggctgc | tcgtctgagc | tggaaccagg | 1140 |
| ttgaccaggt | gatccgtaac | gcgctcgcta | gcccgggttc | tggtggtgac | ctgggtgaag | 1200 |
| ctatccgtga | acagccggaa | caagctcgtc | tcgcgttgac | ccttgctgca | gcggaatctg | 1260 |
| aacgtttcgt | tcgtcagggt | accggtaacg | atgaagctgg | tgcagcgtct | gcggatgtag | 1320 |
| ttagcctgac | ttgcccggtt | gcggctggtg | aatcgctgg | tccggcagac | tctggtgacg | 1380 |
| cgttgcttga | acgtaactac | ccgaccggtg | ctgagttcct | gggtgacggt | ggtgacgtta | 1440 |
| gctttagcac | ccgtggtacc | cagaactgga | ccgttgaacg | tctgctgcag | gctcaccgtc | 1500 |
| agcttgaaga | acgtggttat | gttttcgtag | ttaccacgg | taccttcctg | gaggcggcgc | 1560 |
| agtctatcgt | gttcggtggt | gttcgtgctc | gttcccagga | ccttgacgca | atttggcgcg | 1620 |
| gtttctacat | cgcgggtgac | ccagcgctcg | cgtacggtta | cgctcaggac | caggaaccgg | 1680 |
| atgcgcgtgg | tcgtattcgt | aacggtgcac | tgctgcgtgt | gtacgttcct | cgttctagcc | 1740 |
| tgccgggttt | ctatcgtacc | ggtctgaccc | tggctgcccc | ggaagccgcg | ggtgaagttg | 1800 |

```
aacgtctgat cggtcaccct ctgccgctgc gtctggatgc gatcaccggt ccggaagaag   1860
aaggtggtcg tcttgaaacc atcctgggtt ggccgttggc tgagcgtact gtagtcatcc   1920
cgtctgcgat cccgaccgac ccgcgtaacg taggtggtga ccttgacccg tctagcatcc   1980
cggataaaga acaggccatc agcgcactgc cggactacgc gtctcaaccg ggtaaaccgc   2040
cgcaccacca tcatcaccac aaagatgaac tgtagtgact cgag                    2084
```

<210> SEQ ID NO 4
<211> LENGTH: 669
<212> TYPE: PRT
<213> ORGANISM: Artificial Sequence
<220> FEATURE:
<223> OTHER INFORMATION: Optimized PelB VB4-845 amino acid

<400> SEQUENCE: 4

```
Met Lys Tyr Leu Leu Pro Thr Ala Ala Ala Gly Leu Leu Leu Leu Ala
1               5                   10                  15

Ala Gln Pro Ala Met Ala His His His His His Asp Ile Gln Met
            20                  25                  30

Thr Gln Ser Pro Ser Ser Leu Ser Ala Ser Val Gly Asp Arg Val Thr
        35                  40                  45

Ile Thr Cys Arg Ser Thr Lys Ser Leu Leu His Ser Asn Gly Ile Thr
    50                  55                  60

Tyr Leu Tyr Trp Tyr Gln Gln Lys Pro Gly Lys Ala Pro Lys Leu Leu
65                  70                  75                  80

Ile Tyr Gln Met Ser Asn Leu Ala Ser Gly Val Pro Ser Arg Phe Ser
                85                  90                  95

Ser Ser Gly Ser Gly Thr Asp Phe Thr Leu Thr Ile Ser Ser Leu Gln
            100                 105                 110

Pro Glu Asp Phe Ala Thr Tyr Tyr Cys Ala Gln Asn Leu Glu Ile Pro
        115                 120                 125

Arg Thr Phe Gly Gln Gly Thr Lys Val Glu Leu Lys Arg Ala Thr Pro
    130                 135                 140

Ser His Asn Ser His Gln Val Pro Ser Ala Gly Gly Pro Thr Ala Asn
145                 150                 155                 160

Ser Gly Thr Ser Gly Ser Glu Val Gln Leu Val Gln Ser Gly Pro Gly
                165                 170                 175

Leu Val Gln Pro Gly Gly Ser Val Arg Ile Ser Cys Ala Ala Ser Gly
            180                 185                 190

Tyr Thr Phe Thr Asn Tyr Gly Met Asn Trp Val Lys Gln Ala Pro Gly
        195                 200                 205

Lys Gly Leu Glu Trp Met Gly Trp Ile Asn Thr Tyr Thr Gly Glu Ser
    210                 215                 220

Thr Tyr Ala Asp Ser Phe Lys Gly Arg Phe Thr Phe Ser Leu Asp Thr
225                 230                 235                 240

Ser Ala Ser Ala Ala Tyr Leu Gln Ile Asn Ser Leu Arg Ala Glu Asp
                245                 250                 255

Thr Ala Val Tyr Tyr Cys Ala Arg Phe Ala Ile Lys Gly Asp Tyr Trp
            260                 265                 270

Gly Gln Gly Thr Leu Leu Thr Val Ser Ser Glu Phe Gly Gly Ala Pro
        275                 280                 285

Glu Phe Pro Lys Pro Ser Thr Pro Pro Gly Ser Ser Gly Leu Glu Gly
    290                 295                 300

Gly Ser Leu Ala Ala Leu Thr Ala His Gln Ala Cys His Leu Pro Leu
305                 310                 315                 320
```

Glu Thr Phe Thr Arg His Arg Gln Pro Arg Gly Trp Glu Gln Leu Glu
            325                 330                 335

Gln Cys Gly Tyr Pro Val Gln Arg Leu Val Ala Leu Tyr Leu Ala Ala
            340                 345                 350

Arg Leu Ser Trp Asn Gln Val Asp Gln Val Ile Arg Asn Ala Leu Ala
            355                 360                 365

Ser Pro Gly Ser Gly Gly Asp Leu Gly Glu Ala Ile Arg Glu Gln Pro
            370                 375                 380

Glu Gln Ala Arg Leu Ala Leu Thr Leu Ala Ala Ala Glu Ser Glu Arg
385                 390                 395                 400

Phe Val Arg Gln Gly Thr Gly Asn Asp Glu Ala Gly Ala Ala Ser Ala
            405                 410                 415

Asp Val Val Ser Leu Thr Cys Pro Val Ala Ala Gly Glu Cys Ala Gly
            420                 425                 430

Pro Ala Asp Ser Gly Asp Ala Leu Leu Glu Arg Asn Tyr Pro Thr Gly
            435                 440                 445

Ala Glu Phe Leu Gly Asp Gly Asp Val Ser Phe Ser Thr Arg Gly
            450                 455                 460

Thr Gln Asn Trp Thr Val Glu Arg Leu Leu Gln Ala His Arg Gln Leu
465                 470                 475                 480

Glu Glu Arg Gly Tyr Val Phe Val Gly Tyr His Gly Thr Phe Leu Glu
            485                 490                 495

Ala Ala Gln Ser Ile Val Phe Gly Gly Val Arg Ala Arg Ser Gln Asp
            500                 505                 510

Leu Asp Ala Ile Trp Arg Gly Phe Tyr Ile Ala Gly Asp Pro Ala Leu
            515                 520                 525

Ala Tyr Gly Tyr Ala Gln Asp Gln Glu Pro Asp Ala Arg Gly Arg Ile
            530                 535                 540

Arg Asn Gly Ala Leu Leu Arg Val Tyr Val Pro Arg Ser Ser Leu Pro
545                 550                 555                 560

Gly Phe Tyr Arg Thr Gly Leu Thr Leu Ala Ala Pro Glu Ala Ala Gly
            565                 570                 575

Glu Val Glu Arg Leu Ile Gly His Pro Leu Pro Leu Arg Leu Asp Ala
            580                 585                 590

Ile Thr Gly Pro Glu Glu Glu Gly Gly Arg Leu Glu Thr Ile Leu Gly
            595                 600                 605

Trp Pro Leu Ala Glu Arg Thr Val Val Ile Pro Ser Ala Ile Pro Thr
610                 615                 620

Asp Pro Arg Asn Val Gly Gly Asp Leu Asp Pro Ser Ser Ile Pro Asp
625                 630                 635                 640

Lys Glu Gln Ala Ile Ser Ala Leu Pro Asp Tyr Ala Ser Gln Pro Gly
            645                 650                 655

Lys Pro Pro His His His His His His Lys Asp Glu Leu
            660                 665

<210> SEQ ID NO 5
<211> LENGTH: 339
<212> TYPE: DNA
<213> ORGANISM: Artificial Sequence
<220> FEATURE:
<223> OTHER INFORMATION: Optimized light chain nucleotide

<400> SEQUENCE: 5
gacatccaga tgacccagtc tcctagctct cttagcgcaa gcgtaggtga ccgtgtgacc      60
atcacctgcc gtagcactaa atctctgctg catagcaacg gcatcaccta cctgtattgg     120

```
taccagcaga aaccgggtaa agctccgaaa ctgctgatct accagatgtc taacctggct      180
agcggtgttc ctagccgttt tagctctagc ggtagcggta ctgacttcac cctgaccatt      240
agctctctgc agcctgaaga cttcgcgacc tactactgcg cccagaacct gaaatcccg       300 cgtactttcg gccagggtac caaagtcgaa ctgaaacgt                             339
```

<210> SEQ ID NO 6
<211> LENGTH: 113
<212> TYPE: PRT
<213> ORGANISM: Artificial Sequence
<220> FEATURE:
<223> OTHER INFORMATION: Optimized light chain amino acid

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ser Thr Lys Ser Leu Leu His Ser
                20                  25                  30

Asn Gly Ile Thr Tyr Leu Tyr Trp Tyr Gln Gln Lys Pro Gly Lys Ala
            35                  40                  45

Pro Lys Leu Leu Ile Tyr Gln Met Ser Asn Leu Ala Ser Gly Val Pro
        50                  55                  60

Ser Arg Phe Ser Ser Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Ile Pro Arg Thr Phe Gly Gln Gly Thr Lys Val Glu Leu Lys
            100                 105                 110

Arg
```

<210> SEQ ID NO 7
<211> LENGTH: 348
<212> TYPE: DNA
<213> ORGANISM: Artificial Sequence
<220> FEATURE:
<223> OTHER INFORMATION: Optimized heavy chain nucleotide

<400> SEQUENCE: 7

```
gaagttcagc tcgttcagtc tggtccgggt ctggttcagc cgggtggtag cgttcgtatc      60
tcttgcgcgg cttctggtta caccttcact aactacggta tgaactgggt taaacaggct     120
ccgggtaaag gtctggagtg gatgggttgg attaacacct acacgggtga atctacctac     180
gccgatagct caaaggtcg tttcacccttt agccttgaca cctctgcgtc tgcggcgtac     240
cttcagatca actctctgcg tgctgaggac accgctgttt actactgcgc tcgtttcgcg     300
attaaaggtg actattgggg ccagggcacc ctgctgaccg ttagctct                  348
```

<210> SEQ ID NO 8
<211> LENGTH: 116
<212> TYPE: PRT
<213> ORGANISM: Artificial Sequence
<220> FEATURE:
<223> OTHER INFORMATION: Optimized heavy chain amino acid

<400> SEQUENCE: 8

```
Glu Val Gln Leu Val Gln Ser Gly Pro Gly Leu Val Gln Pro Gly Gly
1               5                   10                  15

Ser Val Arg Ile Ser Cys Ala Ala Ser Gly Tyr Thr Phe Thr Asn Tyr
                20                  25                  30

Gly Met Asn Trp Val Lys Gln Ala Pro Gly Lys Gly Leu Glu Trp Met
```

```
              35                  40                  45
Gly Trp Ile Asn Thr Tyr Thr Gly Glu Ser Thr Tyr Ala Asp Ser Phe
         50                  55                  60

Lys Gly Arg Phe Thr Phe Ser Leu Asp Thr Ser Ala Ser Ala Ala Tyr
 65                  70                  75                  80

Leu Gln Ile Asn Ser Leu Arg Ala Glu Asp Thr Ala Val Tyr Tyr Cys
             85                  90                  95

Ala Arg Phe Ala Ile Lys Gly Asp Tyr Trp Gly Gln Gly Thr Leu Leu
            100                 105                 110

Thr Val Ser Ser
        115

<210> SEQ ID NO 9
<211> LENGTH: 1071
<212> TYPE: DNA
<213> ORGANISM: Artificial Sequence
<220> FEATURE:
<223> OTHER INFORMATION: Optimized Exotoxin A nucleotide

<400> SEQUENCE: 9
gaaggtggta gcttggcagc gttgaccgca caccaagcat gccacctgcc gctggagacc      60
ttcacccgtc accgtcagcc gcgtggttgg gaacagctgg agcagtgcgg ttatccggtt     120
cagcgtctgg tagctctgta cctggctgct cgtctgagct ggaaccaggt tgaccaggtg     180
atccgtaacg cgctcgctag cccgggttct ggtggtgacc tgggtgaagc tatccgtgaa     240
cagccggaac aagctcgtct cgcgttgacc cttgctgcag cggaatctga acgtttcgtt     300
cgtcagggta ccggtaacga tgaagctggt gcagcgtctg cggatgtagt tagcctgact     360
tgcccggttg cggctggtga atgcgctggt ccggcagact ctggtgacgc gttgcttgaa     420
cgtaactacc cgaccggtgc tgagttcctg ggtgacggtg gtgacgttag ctttagcacc     480
cgtggtaccc agaactggac cgttgaacgt ctgctgcagg ctcaccgtca gcttgaagaa     540
cgtggttatg ttttcgtagg ttaccacggt accttcctgg aggcggcgca gtctatcgtg     600
ttcggtggtt tcgtgctcg ttcccaggac cttgacgcaa tttggcgcgg tttctacatc     660
gcgggtgacc cagcgctcgc gtacggttac gctcaggacc aggaaccgga tgcgcgtggt     720
cgtattcgta acggtgcact gctgcgtgtg tacgttcctc gttctagcct gccgggtttc     780
tatcgtaccg gtctgaccct ggctgccccg gaagccgcgg gtgaagttga acgtctgatc     840 ggtcacccctc tgccgctgcg tctggatgcg atcaccggtc cggaagaaga aggtggtcgt     900
cttgaaacca tcctgggttg gccgttggct gagcgtactg tagtcatccc gtctgcgatc     960
ccgaccgacc cgcgtaacgt aggtggtgac cttgacccgt ctagcatccc ggataaagaa    1020
caggccatca gcgcactgcc ggactacgcg tctcaaccgg gtaaaccgcc g             1071

<210> SEQ ID NO 10
<211> LENGTH: 357
<212> TYPE: PRT
<213> ORGANISM: Artificial Sequence
<220> FEATURE:
<223> OTHER INFORMATION: Optimized Exotoxin A amino acid

<400> SEQUENCE: 10

Glu Gly Gly Ser Leu Ala Ala Leu Thr Ala His Gln Ala Cys His Leu
 1               5                  10                  15

Pro Leu Glu Thr Phe Thr Arg His Arg Gln Pro Arg Gly Trp Glu Gln
             20                  25                  30

Leu Glu Gln Cys Gly Tyr Pro Val Gln Arg Leu Val Ala Leu Tyr Leu
```

```
            35                  40                  45
Ala Ala Arg Leu Ser Trp Asn Gln Val Asp Gln Val Ile Arg Asn Ala
 50                  55                  60

Leu Ala Ser Pro Gly Ser Gly Gly Asp Leu Gly Glu Ala Ile Arg Glu
 65                  70                  75                  80

Gln Pro Glu Gln Ala Arg Leu Ala Leu Thr Leu Ala Ala Ala Glu Ser
                 85                  90                  95

Glu Arg Phe Val Arg Gln Gly Thr Gly Asn Asp Glu Ala Gly Ala Ala
                100                 105                 110

Ser Ala Asp Val Val Ser Leu Thr Cys Pro Val Ala Ala Gly Glu Cys
            115                 120                 125

Ala Gly Pro Ala Asp Ser Gly Asp Ala Leu Leu Glu Arg Asn Tyr Pro
        130                 135                 140

Thr Gly Ala Glu Phe Leu Gly Asp Gly Gly Asp Val Ser Phe Ser Thr
145                 150                 155                 160

Arg Gly Thr Gln Asn Trp Thr Val Glu Arg Leu Leu Gln Ala His Arg
                165                 170                 175

Gln Leu Glu Glu Arg Gly Tyr Val Phe Val Gly Tyr His Gly Thr Phe
            180                 185                 190

Leu Glu Ala Ala Gln Ser Ile Val Phe Gly Gly Val Arg Ala Arg Ser
        195                 200                 205

Gln Asp Leu Asp Ala Ile Trp Arg Gly Phe Tyr Ile Ala Gly Asp Pro
210                 215                 220

Ala Leu Ala Tyr Gly Tyr Ala Gln Asp Gln Glu Pro Asp Ala Arg Gly
225                 230                 235                 240

Arg Ile Arg Asn Gly Ala Leu Leu Arg Val Tyr Val Pro Arg Ser Ser
                245                 250                 255

Leu Pro Gly Phe Tyr Arg Thr Gly Leu Thr Leu Ala Ala Pro Glu Ala
            260                 265                 270

Ala Gly Glu Val Glu Arg Leu Ile Gly His Pro Leu Pro Leu Arg Leu
        275                 280                 285

Asp Ala Ile Thr Gly Pro Glu Glu Gly Gly Arg Leu Glu Thr Ile
290                 295                 300

Leu Gly Trp Pro Leu Ala Glu Arg Thr Val Val Ile Pro Ser Ala Ile
305                 310                 315                 320

Pro Thr Asp Pro Arg Asn Val Gly Gly Asp Leu Asp Pro Ser Ser Ile
                325                 330                 335

Pro Asp Lys Glu Gln Ala Ile Ser Ala Leu Pro Asp Tyr Ala Ser Gln
            340                 345                 350

Pro Gly Lys Pro Pro
        355

<210> SEQ ID NO 11
<211> LENGTH: 65
<212> TYPE: DNA
<213> ORGANISM: Artificial Sequence
<220> FEATURE:
<223> OTHER INFORMATION: RBS site sequence

<400> SEQUENCE: 11
gaattcctgc aggtctatgg aacgataaat gcccatgaaa attctatttc aaggagacag    60
tcata                                                                65

<210> SEQ ID NO 12
<211> LENGTH: 66
<212> TYPE: DNA
```

<213> ORGANISM: Artificial Sequence
<220> FEATURE:
<223> OTHER INFORMATION: Optimized PelB nucleotide

<400> SEQUENCE: 12
atgaaatatc tgctgccgac tgctgctgcg ggtctgctgc tgctcgcggc tcagcctgct  60
atggca                                                             66

<210> SEQ ID NO 13
<211> LENGTH: 22
<212> TYPE: PRT
<213> ORGANISM: Artificial Sequence
<220> FEATURE:
<223> OTHER INFORMATION: Optimized PelB amino acid

<400> SEQUENCE: 13

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 14
<211> LENGTH: 18
<212> TYPE: DNA
<213> ORGANISM: Artificial Sequence
<220> FEATURE:
<223> OTHER INFORMATION: Optimized histidine nucleotide

<400> SEQUENCE: 14
caccaccatc accaccat                                                18

<210> SEQ ID NO 15
<211> LENGTH: 6
<212> TYPE: PRT
<213> ORGANISM: Artificial Sequence
<220> FEATURE:
<223> OTHER INFORMATION: Optimized histidine amino acid

<400> SEQUENCE: 15

His His His His His His
1               5

<210> SEQ ID NO 16
<211> LENGTH: 75
<212> TYPE: DNA
<213> ORGANISM: Artificial Sequence
<220> FEATURE:
<223> OTHER INFORMATION: Optimized linker 1 nucleotide

<400> SEQUENCE: 16
gcgaccccga gccataactc tcaccaggtt cctagcgcag gtggtccgac tgctaactct  60
ggcactagcg gttct                                                   75

<210> SEQ ID NO 17
<211> LENGTH: 25
<212> TYPE: PRT
<213> ORGANISM: Artificial Sequence
<220> FEATURE:
<223> OTHER INFORMATION: Optimized linker 1 amino acid

<400> SEQUENCE: 17

Ala Thr Pro Ser His Asn Ser His Gln Val Pro Ser Ala Gly Gly Pro
1               5                   10                  15

Thr Ala Asn Ser Gly Thr Ser Gly Ser
            20                  25

<210> SEQ ID NO 18
<211> LENGTH: 60
<212> TYPE: DNA
<213> ORGANISM: Artificial Sequence
<220> FEATURE:
<223> OTHER INFORMATION: Optimized linker 2 nucleotide

<400> SEQUENCE: 18
gagttcggtg gtgcgcctga gttccctaaa ccgtctaccc cgccaggttc ttctggtctt    60

<210> SEQ ID NO 19
<211> LENGTH: 20
<212> TYPE: PRT
<213> ORGANISM: Artificial Sequence
<220> FEATURE:
<223> OTHER INFORMATION: Optimized linker 2 amino acid

<400> SEQUENCE: 19

Glu Phe Gly Gly Ala Pro Glu Phe Pro Lys Pro Ser Thr Pro Pro Gly
1               5                   10                  15

Ser Ser Gly Leu
            20

<210> SEQ ID NO 20
<211> LENGTH: 42
<212> TYPE: DNA
<213> ORGANISM: Artificial Sequence
<220> FEATURE:
<223> OTHER INFORMATION: Optimized 2nd histidine KDEL nucleotide

<400> SEQUENCE: 20
caccaccatc atcaccacaa agatgaactg tagtgactcg ag                        42

<210> SEQ ID NO 21
<211> LENGTH: 10
<212> TYPE: PRT
<213> ORGANISM: Artificial Sequence
<220> FEATURE:
<223> OTHER INFORMATION: Optimized 2nd histidine KDEL amino acid

<400> SEQUENCE: 21

His His His His His His Lys Asp Glu Leu
1               5                   10

<210> SEQ ID NO 22
<211> LENGTH: 66
<212> TYPE: DNA
<213> ORGANISM: Artificial Sequence
<220> FEATURE:
<223> OTHER INFORMATION: Original PelB

<400> SEQUENCE: 22
atgaaatacc tattgcctac ggcagccgct ggattgttat tactcgctgc ccaaccagcg    60
atggcg                                                                66

<210> SEQ ID NO 23
<211> LENGTH: 18
<212> TYPE: DNA
<213> ORGANISM: Artificial Sequence
<220> FEATURE:
<223> OTHER INFORMATION: Original histidine

<400> SEQUENCE: 23
caccatcatc accatcac                                                   18

<210> SEQ ID NO 24
<211> LENGTH: 339
<212> TYPE: DNA
<213> ORGANISM: Artificial Sequence
<220> FEATURE:
<223> OTHER INFORMATION: Original light chain

<400> SEQUENCE: 24

```
gatatccaga tgacccagtc cccgtcctcc ctgagtgctt ctgttggtga ccgtgttacc    60
atcacctgcc gttccaccaa atccctcctg cactccaacg gtatcaccta cctttattgg   120
tatcaacaga aaccgggtaa agctccgaaa cttctgatct accagatgtc caacctggct   180
tccggtgttc cgtctcgttt ctccagttct ggttctggta ccgacttcac cctgaccatc   240
tcttctctgc agccggaaga cttcgctacc tactactgcg ctcagaacct ggaaatcccg   300
cgtaccttcg gtcagggtac caaagttgaa cttaagcgc                          339
```

<210> SEQ ID NO 25
<211> LENGTH: 75
<212> TYPE: DNA
<213> ORGANISM: Artificial Sequence
<220> FEATURE:
<223> OTHER INFORMATION: Original Linker 1

<400> SEQUENCE: 25

```
gctaccccgt ctcacaactc ccaccaggtt ccatccgcag gcggtccgac tgctaactct    60
ggaactagtg gatcc                                                     75
```

<210> SEQ ID NO 26
<211> LENGTH: 348
<212> TYPE: DNA
<213> ORGANISM: Artificial Sequence
<220> FEATURE:
<223> OTHER INFORMATION: Original heavy chain

<400> SEQUENCE: 26

```
gaagtacagc tggttcagtc cggcccgggt cttgttcaac cgggtggttc cgttcgtatc    60
tcttgcgctg cttctggtta cacgttcacc aactacggca tgaactgggt caaacaggct   120
ccgggtaaag cctggaatg gatgggctgg atcaacacct acaccggtga atccacctac   180
gctgactcct tcaaaggtcg cttcactttc tccctcgaca aagtgctag tgctgcatac   240 ctccaaatca actcgctgcg tgcagaggat acagcagtct attactgcgc ccgtttcgct   300
atcaaaggtg actactgggg tcaaggcacg ctgctgaccg tttcctcg               348
```

<210> SEQ ID NO 27
<211> LENGTH: 60
<212> TYPE: DNA
<213> ORGANISM: Artificial Sequence
<220> FEATURE:
<223> OTHER INFORMATION: Original Linker 2

<400> SEQUENCE: 27

```
gaatttggtg gcgcgccgga gttcccgaaa ccgtccaccc gccgggttc ttctggttta    60
```

<210> SEQ ID NO 28
<211> LENGTH: 1071
<212> TYPE: DNA
<213> ORGANISM: Pseudomonas

<400> SEQUENCE: 28

```
gagggcggca gcctggccgc gctgaccgcg caccaggcct gccacctgcc gctggagact    60
```

```
ttcacccgtc atcgccagcc gcgcggctgg gaacaactgg agcagtgcgg ctatccggtg    120
cagcggctgg tcgccctcta cctggcggcg cgactgtcat ggaaccaggt cgaccaggtg    180
atccgcaacg ccctggccag ccccggcagc ggcggcgacc tgggcgaagc gatccgcgag    240
cagccggagc aggcccgtct ggccctgacc ctggccgccg ccgagagcga gcgcttcgtc    300
cggcagggca ccggcaacga cgaggccggc gcggccagcg ccgacgtggt gagcctgacc    360
tgcccggtcg ccgccggtga atgcgcgggc ccggcggaca cgccgacgc cctgctggag    420 cgcaactatc ccactggcgc ggagttcctc ggcgacggtg gcgacgtcag cttcagcacc    480
cgcggcacgc agaactggac ggtggagcgg ctgctccagg cgcaccgcca actggaggag    540
cgcggctatg tgttcgtcgg ctaccacggc accttcctcg aagcggcgca aagcatcgtc    600
ttcggcgggg tgcgcgcgcg cagccaggat ctcgacgcga tctggcgcgg tttctatatc    660
gccggcgatc cggcgctggc ctacggctac gcccaggacc aggaacccga cgcgcgcggc    720
cggatccgca acggtgccct gctgcgggtc tatgtgccgc gctccagcct gccgggcttc    780
taccgcaccg gcctgaccct ggccgcgccg gaggcggcgg gcgaggtcga acggctgatc    840
ggccatccgc tgccgctgcg cctggacgcc atcaccggcc ccgaggagga aggcgggcgc    900
ctggagacca ttctcggctg gccgctggcc gagcgcaccg tggtgattcc ctcggcgatc    960
cccaccgacc cgcgcaacgt cggtggcgac ctcgacccgt ccagcatccc cgacaaggaa   1020
caggcgatca gcgccctgcc ggactacgcc agccagcccg gcaaaccgcc g            1071

<210> SEQ ID NO 29
<211> LENGTH: 42
<212> TYPE: DNA
<213> ORGANISM: Artificial Sequence
<220> FEATURE:
<223> OTHER INFORMATION: Original HIS/KDEL

<400> SEQUENCE: 29
catcaccacc atcaccataa agacgaactg tagtgactcg ag                         42

<210> SEQ ID NO 30
<211> LENGTH: 30
<212> TYPE: DNA
<213> ORGANISM: Artificial Sequence
<220> FEATURE:
<223> OTHER INFORMATION: Optimized 2nd Histidine KDEL nucleotide

<400> SEQUENCE: 30
caccaccatc atcaccacaa agatgaactg                                       30

<210> SEQ ID NO 31
<211> LENGTH: 30
<212> TYPE: DNA
<213> ORGANISM: Artificial Sequence
<220> FEATURE:
<223> OTHER INFORMATION: Original HIS/KDEL

<400> SEQUENCE: 31
catcaccacc atcaccataa agacgaactg                                       30
```

OPTIMIZED NUCLEIC ACID SEQUENCES FOR THE EXPRESSION OF VB4-845

FIELD OF THE INVENTION

The present application relates to novel nucleic acid sequences for improved recombinant protein expression.

BACKGROUND OF THE INVENTION

VB4-845 is a recombinantly expressed therapeutic protein consisting of a monoclonal antibody specific for the cell surface protein EpCAM linked to a truncated form of pseudomonas exotoxin ((Zangemeister-Wittke et al., 2006) WO04/096271A1, (Zangemeister-Wittke and Di Paolo, 2006) WO06/1635A2). VB4-845 is currently being produced using an E-coli based recombinant protein expression system.

During recombinant protein production in a heterologous system, improper folding of the nascent protein is often the cause of decreased yield of functional protein. Different approaches have been taken to improve folding and expression, including the use of chaperons, changes to the fermentation conditions to affect rate of production and various forms of re-engineering of the expression vector (Vasseur-Godbillon et al., 2006; Endo et al., 2006; Xu et al., 2005; Makrides, 1996; Baneyx et al., 1991).

SUMMARY OF THE INVENTION

The present inventors improved the yield of expression of VB4-845 in an E. coli expression system by modifying the coding and non-coding nucleic acid sequence of the expression vector. More specifically, the modifications include removing major pauses in the open reading frame. A method for modifying nucleic acid sequences to increase translation efficiency is described in U.S. Pat. No. 5,082,767.

The nucleic acid sequence encoding the immunoconjugate was modified in various regions, including regions that encode the $V_H$ region, the $V_L$ region, the PelB leader sequence, the linker sequences, the Histidine sequences, and the KDEL sequences as well as the pseudomonas exotoxin sequence (PE). Accordingly, the present application discloses novel nucleic acid sequences that encode the entire optimized immunotoxin as well as portions thereof which can be used separately or in combination, for example, in the preparation of other immunotoxins.

Other features and advantages of the present application will become apparent from the following detailed description. It should be understood, however, that the detailed description and the specific examples while indicating preferred embodiments of the present application are given by way of illustration only, since various changes and modifications within the spirit and scope of the present application will become apparent to those skilled in the art from this detailed description.

BRIEF DESCRIPTION OF THE DRAWINGS

The invention will now be described in relation to the drawings in which:

FIG. 1 shows the original VB4-845 nucleotide (SEQ ID NO:1) and amino acid (SEQ ID NO:2) sequence.

FIG. 2 shows the optimized VB4-845 nucleotide (SEQ ID NO:3) and amino acid (SEQ ID NO:4) sequence.

FIG. 3 shows the optimized VB4-845 light chain nucleotide (SEQ ID NO:5) and amino acid (SEQ ID NO:6) sequence.

FIG. 4 shows the optimized VB4-845 heavy chain nucleotide (SEQ ID NO:7) and amino acid (SEQ ID NO:8) sequence.

FIG. 5 shows the optimized pseudomonas exotoxin A (ETA) nucleotide (SEQ ID NO:9) and amino acid (SEQ ID NO:10) sequence.

FIG. 6 shows the optimized RBS sequence, PelB leader sequences, histidine sequences, and linker sequences of the VB4-845 constructs (SEQ ID NOS: 11 to 21 and 30).

FIG. 7 shows a comparison of the optimized VB4-845 nucleotide sequences compared with the original VB4-845 nucleotide sequences (SEQ ID NOS: 22 to 29 and 31). Changes in the nucleotide sequences are shown in bold and are underlined in the original sequence.

DETAILED DESCRIPTION OF THE INVENTION

A. Definitions

Figure 8:
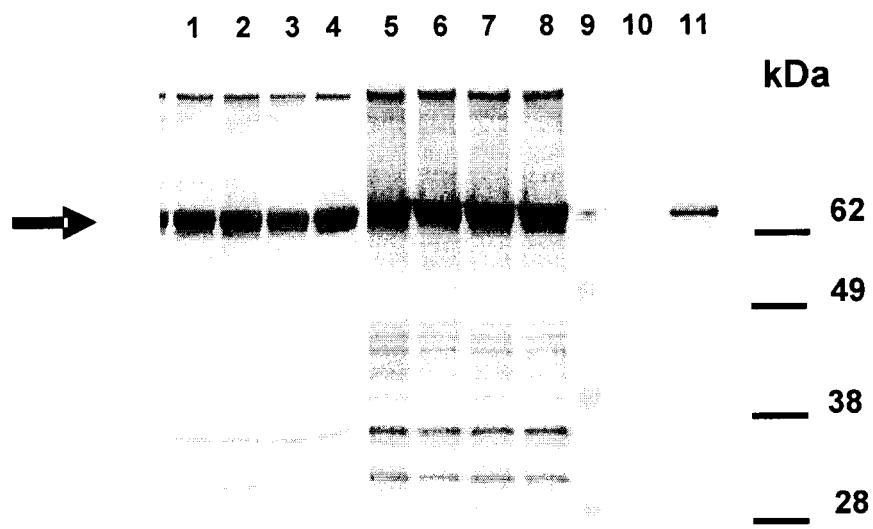
FIG. 8 is a Western blot showing original VB4-845 and VB4-845 optimized protein expression from small scale expression in either GMM or Xoma bacterial strains.

The term "a cell" includes a single cell as well as a plurality or population of cells. Administering an agent to a cell includes both in vitro and in vivo administrations.

The term "amino acid" includes all of the naturally occurring amino acids as well as modified amino acids.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and Domain Antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

The term "binding protein" as used herein refers to proteins that specifically bind to another substance such as an antigen. In an embodiment, binding proteins are antibodies or antibody fragments.

By "biologically compatible form suitable for administration in vivo" is meant a form of the substance to be administered in which any toxic effects are outweighed by the therapeutic effects.

The phrase "detecting or monitoring cancer" refers to a method or process of determining if a subject has or does not have cancer, the extent of cancer, the severity of cancer and/or grade of cancer.

As used herein, the phrase "effective amount" means an amount effective, at dosages and for periods of time necessary to achieve the desired result. Effective amounts of an immunoconjugate may vary according to factors such as the disease state, age, sex, weight of the animal. Dosage regime may be adjusted to provide the optimum therapeutic response. For example, several divided doses may be administered daily or the dose may be proportionally reduced as indicated by the exigencies of the therapeutic situation.

The term "heavy chain variable region" as used herein refers to the variable region of a heavy chain of an antibody molecule. The heavy chain variable region has three complementarity determining regions (CDRs) termed heavy chain complementarity determining region 1, heavy chain complementarity determining region 2 and heavy chain complementarity determining region 3 from the amino terminus to carboxy terminus.

The term "immunoconjugate" as used herein comprises (1) a binding protein attached to (2) an effector molecule.

The term "immunotoxin" as used herein comprises (1) a binding protein attached to (2) a toxin.

The term "isolated nucleic acid sequences" as used herein refers to a nucleic acid substantially free of cellular material or culture medium when produced by recombinant DNA techniques.

The term "light chain variable region" as used herein refers to the variable region of a light chain of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The term "nucleic acid" is intended to include DNA and RNA and can be either double stranded or single stranded, and represents the sense or antisense strand.

As used herein, the phrase "treating cancer" refers to inhibition of cancer cell replication, inhibition of cancer spread (metastasis), inhibition of tumor growth, reduction of cancer cell number or tumor growth, decrease in the malignant grade of a cancer (e.g., increased differentiation), or improved cancer-related symptoms.

B. Nucleic Acid Molecules

As mentioned previously, the nucleic acid sequences encoding the VB4-845 immunotoxin were modified and resulted in increased expression of the immunotoxin as described in the Examples. The present application includes all of the novel, modified nucleic acid sequences. In particular, the present application includes the following novel nucleic acid sequences:

the $V_H$ region shown in SEQ ID NO:7 (FIG. 4);
the $V_L$ region shown in SEQ ID NO:5 (FIG. 3);
the pseudomonas exotoxin A sequence shown in SEQ ID NO:9 (FIG. 5);
the VB4-845 sequence shown in SEQ ID NO:3 (FIG. 2);
the PelB leader sequence shown in SEQ ID NO:12 (FIG. 6);
the first and second histidines sequences including KDEL shown in SEQ ID NOS:14, 20 and 30 (FIG. 6); and
the linker sequences shown in SEQ ID NOS:16 and 18 (FIG. 6).

A person skilled in the art will appreciate that the novel nucleic acid sequences of the present application can be used in a number of recombinant methods.

Accordingly, the nucleic acid sequences of the present application may be incorporated in a known manner into an appropriate expression vector which ensures good expression of the proteins encoded thereof. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the present application and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The present application therefore contemplates a recombinant expression vector of the present application containing a nucleic acid molecule of the present application, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in (Goeddel, 1990), Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the present application may also contain a selectable marker gene which facilitates the selection of host cells transformed or transfected with a recombinant molecule of the present application. Examples of selectable marker genes are genes encoding a protein such as G418 and hygromycin which confer resistance to certain drugs, (3-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the present application and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the present application. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in (Sambrook et al., 2001) (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the present application may be expressed in yeast cells or mammalian cells. Other suitable host cells can be found in (Goeddel, 1990), Gene Expression Technology: Methods in Enzymology 185, Academic Press, San Diego, Calif. (1991). In addition, the proteins of the present application may be expressed in prokaryotic cells, such as *Escherichia coli* (Zhang et al., 2004), Science 303(5656): 371-3). In addition, a *Pseudomonas* based expression system such as *Pseudomonas fluorescens* can be used (US Patent Application Publication No. US 2005/0186666, (Schneider et al., 2005)).

Yeast and fungi host cells suitable for carrying out the present application include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 ((Baldari et al., 1987), Embo J. 6:229-234), pMFa ((Kurjan and Herskowitz, 1982), Cell 30:933-943 (1982)), pJRY88 ((Schultz et al., 1987), Gene 54:113-123), and pYES2 (Invitrogen Corporation, San Diego, Calif.). Protocols for the transformation of yeast and fungi are well known to those of ordinary skill in the art (see (Hinnen et al., 1978) Proc. Natl. Acad. Sci. USA 75:1929); ((Ito et al., 1983), J. Bacteriology 153:163) and ((Cullen et al., 1987) BioITechnology 5:369).

Mammalian cells suitable for carrying out the present application include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 ((Seed, 1987), Nature 329:840) and pMT2PC ((Kaufman et al., 1987), EMBO J. 6:187-195).

Given the teachings provided herein, promoters, terminators, and methods for introducing expression vectors of an appropriate type into plant, avian, and insect cells may also be readily accomplished. For example, within one embodiment, the proteins of the present application may be expressed from plant cells (see (Sinkar et al., 1987), J. Biosci (Bangalore) 11:47-58), which reviews the use of *Agrobacterium rhizogenes* vectors; see also ((Zambryski et al., 1984), Genetic Engineering, Principles and Methods, Hollaender and Setlow (eds.), Vol. VI, pp. 253-278, Plenum Press, New York), which describes the use of expression vectors for plant cells, including, among others, PAPS2022, PAPS2023, and PAPS2034).

Insect cells suitable for carrying out the present application include cells and cell lines from *Bombyx, Trichoplusia* or *Spodotera* species. Baculovirus vectors available for expression of proteins in cultured insect cells (SF 9 cells) include the pAc series ((Smith et al., 1983), Mol. Cell. Biol. 3:2156-2165) and the pVL series ((Luckow and Summers, 1989), Virology 170:31-39). Some baculovirus-insect cell expression systems suitable for expression of the recombinant proteins of the present application are described in PCT/US/02442.

Alternatively, the proteins of the present application may also be expressed in non-human transgenic animals such as rats, rabbits, sheep and pigs ((Hammer et al., 1985). Nature 315:680-683); (Brinster et al., 1985; Palmiter and Brinster, 1985; Palmiter et al., 1983) Science 222:809-814); and ((Leder and Stewart, 1988) U.S. Pat. No. 4,736,866).

Accordingly, the present application provides a recombinant expression vector comprising one or more of the novel nucleic acid sequences (i.e. SEQ ID NOS:3, 5, 7, 9, 12, 14, 16, 18, 20 and/or 30) as well as methods and uses of the expression vectors in the preparation of recombinant proteins. Further, the application provides a host cell comprising one or more of the novel nucleic acid sequences or expression vectors comprising one or more of the novel nucleic acid sequences.

C. Binding Proteins

The present application also includes binding proteins comprising one or more of the amino acid sequences encoded by the novel nucleic acid sequences disclosed herein (i.e. SEQ ID NOS:3, 5, 7, 9, 12, 14, 16, 18, 20 and/or 30).

In one embodiment, the binding protein comprises one or more of the amino acid sequences encoded by the nucleic acid sequences selected from the group consisting of: the $V_H$ region shown in SEQ ID NO:7 and the $V_L$ region shown in SEQ ID NO: 5.

The present application also includes the use of the novel nucleic acid sequences for the preparation of binding proteins and methods thereof.

The present application also provides a nucleic acid sequence that comprise one or more of the novel nucleic acid sequences disclosed above (i.e. SEQ ID NOS:3, 5, 7, 9, 12, 14, 16, 18, 20 and/or 30) and encodes a binding protein. In one embodiment, the nucleic acid sequence comprises one or more of the nucleic acid sequences selected from the group consisting of: the $V_H$ region shown in SEQ ID NO:7 and the $V_L$ region shown in SEQ ID NO: 5.

The present application includes the use of the binding proteins disclosed herein in any and all applications including diagnostic and therapeutic applications. In one embodiment, the binding proteins are used for detecting or monitoring cancer. In another embodiment, the binding proteins are used for treating cancer.

D. Immunoconjugates

The present application includes the use of the binding proteins to prepare an immunoconjugate and methods thereof. Accordingly, the present application provides an immunoconjugate comprising (1) a binding protein disclosed herein, preferably an antibody or antibody fragment, attached to (2) an effector molecule. In one embodiment, the binding protein of the present application binds to an antigen or molecule on or in a cancer cell.

In one embodiment the effector molecule is (i) a label, which can generate a detectable signal, directly or indirectly, or (ii) a cancer therapeutic agent, which is either cytotoxic, cytostatic or otherwise prevents or reduces the ability of the cancer cells to divide and/or metastasize.

In one embodiment, the immunoconjugate is internalized and the cancer therapeutic agent is a cytotoxin that blocks the protein synthesis of the cell, therein leading to cell death. Importantly, since most normal cells do not widely express the antigen present on the cancer cells, they cannot bind and internalize the immunoconjugate, and are protected from the killing effect of the toxin or other cancer therapeutic agents.

A variety of effector molecules may be used and a number of such effector molecules are intracellularly active molecules. Accordingly, in an embodiment, the immunoconjugate is internalized by the cancer cell.

In preferred embodiments, the effector molecule is a cancer therapeutic agent, more preferably a cytotoxin that comprises a polypeptide having ribosome-inactivating activity including, without limitation, gelonin, bouganin, saporin, ricin, ricin A chain, bryodin, diphtheria toxin, restrictocin, *Pseudomonas* exotoxin A and variants thereof. When the protein is a ribosome-inactivating protein, the immunoconjugate must be internalized upon binding to the cancer cell in order for the protein to be cytotoxic to the cells. Accordingly, in an embodiment, the effector molecule is a cytotoxin and the immunoconjugate is internalized by the cancer cell.

In one embodiment, the toxin is bouganin or *Pseudomonas* exotoxin A, and variants thereof. In another embodiment, the toxin is modified bouganin or a truncated form of *Pseudomonas* exotoxin A that lacks the cell binding domain. In a further embodiment, the toxin is a bouganin substantially devoid of T-cell epitopes or a truncated form of *Pseudomonas* exotoxin A that consists of amino acids 252-608.

In one embodiment, the immunoconjugate comprises a pseudomonas exotoxin A encoded by the nucleic acid sequence shown in SEQ ID NO:9. In another embodiment, the immunoconjugate comprises the amino acid sequence encoded by the nucleic acid sequence shown in SEQ ID NO:3.

The present application also includes the pseudomonas exotoxin A nucleic acid sequence shown in SEQ ID NO: 9 and its use in the preparation of immunotoxins. Accordingly the present application comprises an immunotoxin comprising (1) a binding protein attached to (2) a exotoxin A encoded by the nucleic acid sequence shown in SEQ ID NO:9.

The binding protein is preferably an antibody or antibody fragment that binds to a cancer associated antigen. In one embodiment, the cancer associated antigen is but not limited to EpCAM, a variant of mammalian Scratch ((Chahal et al., 2007) WO 2007/071051A1), CD44E, a variant of mammalian alpha feto protein (AFP) ((Glover et al., 2005) WO 2005/121341), a variant of Glut 8 ((Glover et al., 2006) WO 2006/066408), PSCA (prostate stem cell antigen), Mesothelin, CD25, EGFR (epidermal growth factor), High Molecular Weight Melanoma Associated Antigen, or CD22.

In other nonlimiting embodiments, the cancer therapeutic agent comprises an agent that acts to disrupt DNA. Thus, the cancer therapeutic agents may be selected, without limitation, from enediynes (e.g., calicheamicin and esperamicin) and non-enediyne small molecule agents (e.g., bleomycin, methidiumpropyl-EDTA-Fe(II)). Other cancer therapeutic agents include, without limitation, daunorubicin, doxorubicin, distamycin A, cisplatin, mitomycin C, ecteinascidins, duocarmycin/CC-1065, and bleomycin/pepleomycin.

In other nonlimiting embodiments, the cancer therapeutic agent comprises an agent that acts to disrupt tubulin. Such agents may comprise, without limitation, rhizoxin/maytansine, paclitaxel, vincristine and vinblastine, colchicine, auristatin dolastatin 10 MMAE, and peloruside A.

In other nonlimiting embodiments, the cancer therapeutic portion of the immunoconjugate may comprise an alkylating agent including, without limitation, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In other nonlimiting embodiments, the cancer therapeutic agent portion of the immunoconjugate may comprise an antimitotic agent including, without limitation, allocolchicine NSC 406042, Halichondrin B NSC 609395, colchicine NSC 757, colchicine derivative NSC 33410, dolastatin 10 NSC 376128 (NG—auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In other nonlimiting embodiments, the cancer therapeutic agent portion of the immunoconjugate may comprise an topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In other nonlimiting embodiments, cancer therapeutic agent portion of the immunoconjugate may comprise an topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In other nonlimiting embodiments, the cancer therapeutic agent portion of the immunoconjugate may comprise an RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, alpha-TGDR NSC 71851, aphidicolin glycinate NSC 303812, ara-C NSC 63878, 5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

In another nonlimiting embodiment, the therapeutic portion of the immunoconjugates may be a nucleic acid. Nucleic acids that may be used include, but are not limited to, antisense RNA, genes or other polynucleotides, nucleic acid analogs such as thioguanine and thiopurine.

The present application also provides a method of treating or preventing cancer, comprising administering to a patient suspected of having cancer an effective amount of the immunoconjugate of the present application, wherein the effector molecule is a cancer therapeutic agent. In another embodiment, the present application provides the use of an effective amount of the immunoconjugate of the present application, wherein the effector molecule is a cancer therapeutic agent, for the manufacture of a medicament for treating or preventing cancer. Furthermore, the present application provides the use of an effective amount of the immunoconjugate of the present application, wherein the effector molecule is a cancer therapeutic agent, comprising the use of an additional cancer therapeutic for the manufacture of a medicament for simultaneous, separate or sequential treatment or prevention of cancer.

The combination of one or more immunoconjugates and one or more other cancer therapies may synergistically act to combat the tumor or cancer. The other cancer therapies include, without limitation, other cancer therapeutic agents including, without limitation, 2,2,2 trichlorotriethylamine, 3-HP, 5,6-dihydro-5-5-azacytidine, 5-aza-2'-deoxycytidine, 5-azacytidine, 5-fluorouracil, 5-HP, 5-propagermanium, 6-azauridine, 6-diazo-5-0x0-L-norleucine, 6-mercaptopurine, 6-thioguanine, abrin, Aceglarone, acivicin, Aclacinomycin, actinomycin, actinomycin D, aldesleukin, allocolchicine, allutamine, alpha-fetoprotein, alpha-TGDR, Altretamine, aminocamptothecin, Aminoglutethimide, aminopterin derivative, amonafide, amsacrine, an antifol, anastrozole, ancitabine, angiogenin antisense oligonucleotide, angiostatin, anthramycin, anthrapyrazole derivative, antithrombin, aphidicolin glycinate, ara-C, asparaginase, auristatin, autologous cells or tissues, Avastin, azacitidine, azaserine, aziridine, AZQ, *Bacillus*, Baker's soluble antifol, batimastat, BCG live vaccine, bcl-2 antisense oligonucleotide, BCNU, benzodepa, betamethasone, beta-TGDR, biaomycin, bicalutamide, bisantrene, bleomycin, brequinar, buserelin, Busulfan, cactinomycin, calicheamicin, calusterone, campath-1, camptothecin, camptothecin Na salt, capecitabine, carboplain, Carboplatin, carboquone, carboxyphthalatoplatinum, carcinoembryonic antigen, carmofur, carmustine, carnptothecin derivatives, carubicin, carzinophilin, CBDCA, CCNU, CHIP, Chlorabusin, Chlorambucil, chlormadinone acetate, chlornaphazine, chlorozotocin, chromomycins, cisplatin, cisplatinum, cladribine, clomesone, colchicine, colchicine derivative, collagen 14-amino acid peptide, cortisol, cortisone, cyanomorpholinodoxorubicin, cyclarabine, cyclocytidine, cyclodisone, cyclophosphamide, cyclothosphamide, cytarabine, cytochalasin B, cytosine arabinoside, dacarbazine, daclinomycin, dactinomycin, Dasatinib, daunorubicin, defosfamide, dehydrotestosterone, demecolcine, denopterin, deoxydoxorubicin, dexamethasone, dianhydrogalactitol, diaziquone, dichlorallyl lawsone, diphtheria toxin, distamycin A, Docetaxel, dolastatin 10, doxifluridine, doxorubicin, droloxifene, dromostanolone, Duocarmycin/CC-1065, ecteinascidins, edatrexate, eflomithine, elliptinium acetate, emetine, emitefur, endostatin, enocitabine, epipodophyllotoxin, epirubicin, epitiostanol, erbitux, Erlotinib, esperamicin, estramustine, estrogen, ethidium bromide, etoglucid, etoposide, Fadrozole, Fenretinide, fibronectin 29 kDa N-terminal proteolytic fragment, Fibronectin 40 kDa C-terminal N-terminal proteolytic fragment, florafbr (pro-drug), floxuridhe, floxuridine, fludarabine, fluorodopan, flutamide, folinic acid, formestane, fosfestrol, fotemustine, gallium nitrate, Gefitinib, gemcitabine, gemcitibine, gemtuzumab, glucocorticoid, goserelin, gramicidin D, granulocyte monocyte colony stimulating factor, guanazole NSC 1895, Guerin, Halichondrin B, hepsulfam, hexamethylmelamine, hexestrol, human chorionic gonadotropin, hycanthone, hydroxyurea, idarubicin, Ifosamide, Imatinib, improsulfan, inosine glycodialdehyde, interferon, interferon-alpha, interferon-beta, interferon-gamma, interleukin-12, interleukin-15, interleukin-18, interleukin-1, interleukin-2, interleukin-2, interleukin-6, interleukins, Irinotecan, iubidazone, kringle 5, L-alanosine, Lapatinib, L-asparaginase, lauprolide acetate, lentinan, letrozole, leuprolide, leuprolide acetate (LUPRON), levamisole, lidocaine, liposomal dihydroxyanthracindione, lomusline, lomustine, lonidamine, lymphokines, lymphotoxin, LYSODREN, macbecin, macrophage inflammatory protein, m-AMSA, mannomustine, maytansine, mechlorethamine, mechlorethamine oxide hydrochloride, medroxyprogesterone, megestrol acetate, melanocyte lineage proteins, melengestrol, melphalan, menogaril, mepitiostane, mercaptopurine, mesna, methidiumpropyl-EDTA-Fe(II)), methotrexate, methotrexate derivative, meturedepa, miboplatin, miltefosine, mineral corticoid, mithramycin, mitobronitol, mitoguazone, mitolactol, mitolanc, mitomycin C, mitotane, mitoxantrone, mitozolamide, mopidamol, morpholinodoxorubicin, mutated tumor-specific antigens, mycophenolic acid, N-(phosphonoacetyl)-L-aspartate (PALA), N,N-dibenzyl daunomycin, nerve growth factor, Nilotinib, nilutamide, nimustine, nitracine, nitrogen mustard, nogalamycin, nonautologous cells or tissues, novembichin, olivomycins, ontak, Onyx-015, oxaliplatin, oxanthrazole, paclitaxel, PCNU, pegaspergase, pelomside A, pentostatin, peplomycin, perfosfamide, phenamet, phenesterine, picamycin, piperazine, piperazinedione, pipobroman, piposulfan, pirarubicin, piritrexim, platelet derived growth factor, platelet factor-4 7.8 kDa proteolytic fragment, platelet factor-4 13 amino acid peptide, plicamycin, podophyllinic acid 2-ethylhydrazide, podophyllotoxin, polyestradiol phosphate, porfimir, porfiromycin, prednimustine, prednisone, procabazine, procaine, progestine, prolactin 16 kDa proteolytic fragment, propranolol, *Pseudomonas* exotoxin, PSK, pteropterin, puromycin, pyrazofurin, pyrazoloacridine, pyrazoloimidazole, Ranimustine, razoxane, retinoid, rhizoxin, rhizoxinlmaytansine, ricin A, rituxan, rituximab, riuxlmab, Roquinimex, Serpin (Serine Protease Inhibitor), Sizofican, sobuzoxane, Sorafenib, SPARC, 20-amino acid peptide, Spirogermanium, spirohydantoin mustard, straplozocin, streptonigrin, streptozocin, Sunitinib, Tamoxifen, Taxol, Taxol derivative, tegafur, temozoamide, teniposide, tenuazonic acid, teroxirone, testolactone, tetracaine, tetraplatin, thalidomide, Thiamiprine, thiocolchicine, thioepa, thiopurine, thio-tepa, Thrombospondin I 19 amino acid peptide, tissue plasminogen activator, Tomudex, topotecan, toremifene, trastuzutmaban, tretinoin, triaziquone, triethylenemelamine, triethylenephosphoramide, triethylenethiophosphoramide, trilostane, trimetrexate, triptorelin, trityl cysteine, trofosfamide, Trontecan, tubercidin, tumor necrosis factor-like cytokine, tumor necrosis factors, Ubenimex, uracil mustard, uracil nitrogen mustard, uredepa, urethan, Vandetanib (ZD6474), VEGF antisense oligonucleotide, vinblastine, vinblastine sulfate, vincristine, vincristine sulfate, vindesine, vinorelbine, VM-26, VP-16, Yoshi-864, Zinostatin, zorubicin.

In another embodiment, one or more immunoconjugates of the disclosed herein can be administered in combination with one or more of the following cancer therapies or categories of therapeutic agents, including without limitation, radiation, surgery, gene therapy, agents to control of side effects (eg. antihistaminic agents, anti-nausea agents), cancer vaccines, inhibitors of angiogenesis, immune modulators, anti-inflammatories, immunosuppressants, agents that increase expression of antigen, other agents associated with cancer therapy chemotherapeutic agents (i.e. immunotherapeutics, photosensitizers, tk inhibitors, antibiotics, antimetabolites, agents that acts to disrupt DNA, agents that acts to disrupt tubulin, alkylating agents, topoisomerase I inhibitors topoisomerase II inhibitors, cytokines and growth factors, hormonal therapies, vinca alkyloids, plant alkaloids, anti-mitotic agents).

In one embodiment of the present application, cancer includes, without limitation, cervical cancer, uterine cancer, ovarian cancer, pancreatic cancer, kidney cancer, gallbladder cancer, liver cancer, head and neck cancer, squamous cell carcinoma, gastrointestinal cancer, breast cancer (such as carcinoma, ductal, lobular, and nipple), prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, colon cancer, rectum cancer, stomach cancer, bladder cancer, pancreatic cancer, endometrial cancer, plasmacytoma, lymphoma, and melanoma. In a preferred embodiment, the cancer includes, without limitation, bladder cancer, breast cancer, cervical cancer, colon cancer, kidney cancer, liver cancer, lung cancer, ovarian cancer, pancreatic cancer, prostate cancer, rectal cancer, skin cancer, stomach cancer, uterine cancer, and head and neck cancer.

The ability of the immunoconjugate of the present application to selectively inhibit or destroy cancerous cells may be readily tested in vitro using cancer cell lines. The selective inhibitory effect of the immunoconjugates of the present application may be determined, for example by demonstrating the selective inhibition of cellular proliferation of the cancer cells.

Toxicity may also be measured based on cell viability, for example, the viability of cancer and normal cell cultures exposed to the immunoconjugate may be compared. Cell viability may be assessed by known techniques, such as trypan blue exclusion assays.

In another example, a number of models may be used to test the effectiveness of the immunoconjugates of the present application. (Thompson et al., 1994) has described a model for the determination of invasiveness of human breast cancer cells in vitro by measuring tumor cell-mediated proteolysis of extracellular matrix and tumor cell invasion of reconstituted basement membrane (collagen, laminin, fibronectin, Matrigel or gelatin). Other applicable cancer cell models include cultured ovarian adenocarcinoma cells (Young et al., 1996; Moore et al., 1997), human follicular thyroid cancer cells (Demeure et al., 1992) human melanoma (A-2058) and fibrosarcoma (HT-1080) cell lines (Mackay et al., 1994), and lung squamous (HS-24) and adenocarcinoma (SB-3) cell lines (Spiess et al., 1994). An in vivo test system involving the implantation of tumors and measurement of tumor growth and metastasis in athymic nude mice has also been described (Thompson et al., 1994; Shi et al., 1993).

The immunoconjugates of the present application may be formulated into pharmaceutical compositions for administration to subjects in a biologically compatible form suitable for administration in vivo. The substances may be administered to living organisms including humans, and animals. Administration of a therapeutically active amount of the pharmaceutical compositions of the present application is defined as an amount effective, at dosages and for periods of time necessary to achieve the desired result. For example, a therapeutically active amount of a substance may vary according to factors such as the disease state, age, sex, and weight of the individual, and the ability of the recombinant protein of the present application to elicit a desired response in the individual. Dosage regime may be adjusted to provide the optimum therapeutic response. For example, several divided doses may be administered daily or the dose may be proportionally reduced as indicated by the exigencies of the therapeutic situation.

Accordingly, the present application provides a pharmaceutical composition for treating or preventing cancer comprising the immunoconjugates of the present application, and a pharmaceutically acceptable carrier, diluent or excipient. In a preferred embodiment, the effector molecule of the immunoconjugate in the pharmaceutical composition is a cancer therapeutic agent, more preferably a toxin.

The pharmaceutical preparation comprising the immunoconjugate of the present application may be administered systemically. The pharmaceutical preparation may be administered directly to the cancer site. Depending on the route of administration, the immunoconjugate may be coated in a material to protect the compound from the action of enzymes, acids and other natural conditions that may inactivate the compound.

In accordance with one aspect of the present application, the immunoconjugate is delivered to the patient by direct administration. The present application contemplates the pharmaceutical composition being administered in at least an amount sufficient to achieve the endpoint, and if necessary, comprises a pharmaceutically acceptable carrier.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Gennaro, 2000); Remington's Pharmaceutical Sciences, Mack Publishing Company, Easton, Pa., USA 1985. On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, alcohols, polyols, glycerin and vegetable oils, for example. Extemporaneous injection solutions and suspensions may be prepared from sterile powders, granules, tablets, or concentrated solutions or suspensions. Immunoconjugate may be supplied, for example but not by way of limitation, as a lyophilized powder which is reconstituted with sterile water or saline prior to administration to the patient.

The present application also provides a nucleic acid sequence that comprises one or more of the novel nucleic acid sequences of the present application (.e. SEQ ID NO:3, 5, 7, 9, 12, 14, 16, 18, 20 and/or 30) and encodes an immunoconjugate. In one embodiment, the nucleic acid sequence comprises one or more of the nucleic acid sequences selected from the group consisting of: the $V_H$ region shown in SEQ ID NO:7; the $V_L$ region shown in SEQ ID NO: 5; the nucleic acid sequence shown in SEQ ID NO:9 and; the nucleic acid sequence shown in SEQ ID NO:3.

E. Leader Sequences

The present application also includes the modified leader sequences. In one embodiment, the modified leader sequence is encoded by the nucleic acid sequence shown in SEQ ID NO:12 or comprises the amino acid sequence shown in SEQ ID NO:13. Such leader sequences can be used to optimize the expression of other recombinant proteins including immunoconjugates as described above.

F. Linker Sequences

The present application also includes modified linker sequences. In particular, the present application includes the modified linker sequences encoded by the nucleic acid sequences shown in SEQ ID NO:16 and/or 18. The modified linker sequence can be used in the preparation of other conjugates including immunoconjugates, more preferably, immunotoxins.

G. *Pseudomonas* Exotoxin A Sequences

The present application also includes modified pseudomonas exotoxin A sequences. In particular, the present application includes the pseudomonas exotoxin A encoded by the nucleic acid sequence shown in SEQ ID NO:9 or comprises the amino acid sequence shown in SEQ ID NO:10. Such modified pseudomonas exotoxin A sequences can be used in the preparation of other conjugates, including immunotoxins.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLES

Example 1

Evaluation of Improved Recombinant Expression

The expression level of a VB4-845 optimized clone was evaluated The optimized VB4-845 insert was ligated into the pING3302 plasmid, transformed in two different strains of *E. coli* E104 competent cells and selected on LB-agar plate containing 25 μg/mL of tetracycline. The first strain of *E. coli* E104 was provided by Xoma while the second strain was selected in-house for growth in GMM media. The insert was sequenced to ensure that the optimization at the nucleotide level did not change the amino acid sequence. The sequences of the original VB4-845 construct and the optimized VB4-845 construct are shown in FIGS. 1 and 2, respectively.

The two transformed E104 strains containing VB4-845 and VB4-845-optimized constructs were propagated in 30 mL of TB media (1% inoculum) in a 250 mL shake flask at 25° C. and shaken at 225 rpm for approximately 8 hours until the optical density (O.D. 600 nm) reached 1.2. At this time, the culture was induced with a final concentration of 0.1% L- (+) arabinose and incubated at 25° C. for 16 hours. Subsequently, the supernatant was collected by centrifugation at 14000 rpm for 5 minutes and analyzed by Western blot using a rabbit anti-PE (1/5000) followed by a goat anti-rabbit HRP antibody (1/2000) under reducing or non-reducing conditions to confirm the presence and size of the VB4-845 protein.

The Western blot analysis of both induced *E. coli* E104 strains transformed with the VB4-845 optimized constructs showed a higher level of expression of the full length protein compared to the non-optimized VB4-845 (FIG. 8). Western blotting of non-induced E104 culture supernatant revealed no corresponding bands indicating that these proteins are specifically detected with the corresponding antibody (FIG. 8, lane 10).

Figure 9:
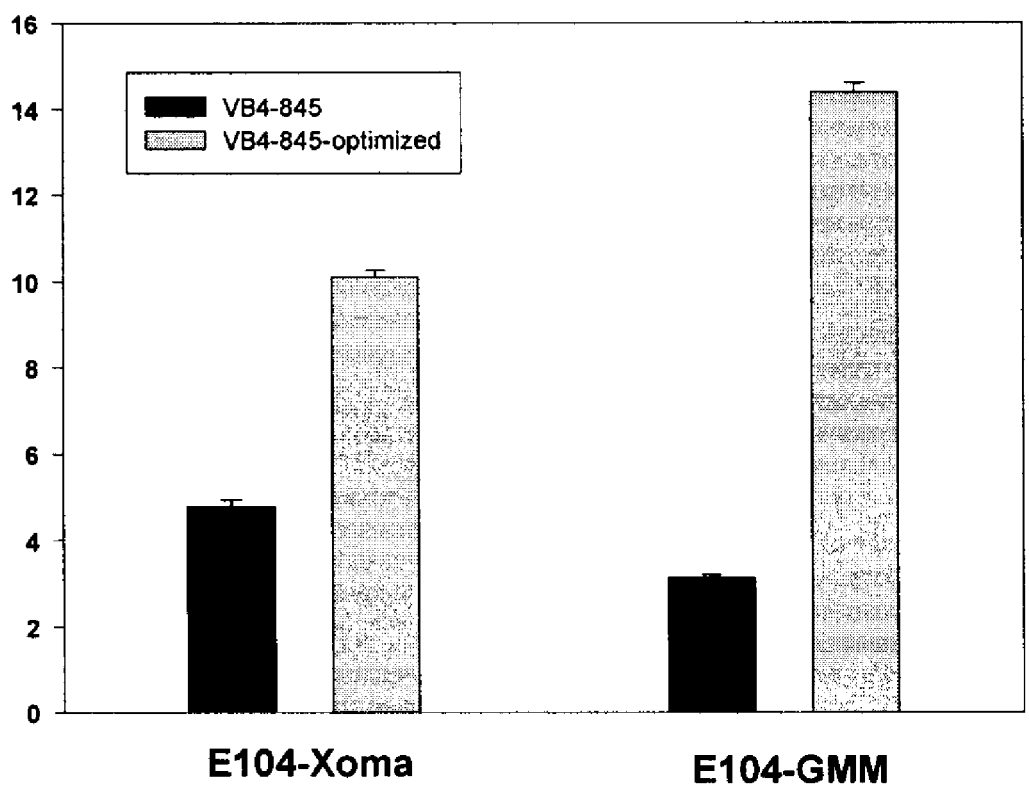
FIG. 9 is a graph showing the ELISA quantification of soluble VB4-845 protein expression from both Xoma and GMM bacterial strains. Supernatents of VB4-845 and VB4-845 optimized clones grown and induced in a shake flask containing TB media were collected 16 hours post-induction and quantified by ELISA.

The protein expression level of VB4-845-optimized clones in both *E. coli* E104 strains was quantified by ELISA and compared to the non-optimized VB4-845. An Immulon microtitre plate was coated overnight with 100 μL of rabbit anti-PE diluted at 10 μg/mL After three washes with PBS/ 0.5% Tween 20, the plate was blocked with 1% BSA for 1 hour at room temperature. TB samples, 100 μL, diluted at 1/50, 1/500, 1/1000, 1/2000, 1/4000 and 1/8000 were added to the plate and incubated for 2 hours at room temperature. Purified VB4-845, diluted at 12.5 to 0.8 ng/mL, was used to generate the standard curve. VB4-845 at a known concentration, 10 and 5 ng, and non-induced supernatant were used as positive and negative controls, respectively. After the incubation, the plate was washed as above and incubated with the second antibody, a rabbit anti-4D5 biotynilated diluted at 5 μg/mL in dilution buffer. After 1 hour incubation, the plate was washed and incubated with 100 μL of streptavidin-HRP diluted at 1/1000 was added for 30 minutes at room temperature. The reaction was developed in presence of TMB substrate for 2 minutes and stopped with 1N phosphoric acid. The plate was read at a wavelength of 405 nm using the Softmax Pro software. The level of expression of the VB4-845-optimized in E104-Xoma and E104-GMM strains was 2 and 4 times higher than the non-optimized VB4-845, respectively (FIG. 9).

Example 2

Modified of Fermentation and Production of VB4-845 Optimized Fermentation Media

*E. coli* cultivation was performed in either 2 L or 15 L bioreactor working volumes in glycerol minimal media (GMM) containing: ammonium sulfate (13 g/L), potassium phosphate monobasic (1.7 g/L), potassium phosphate dibasic (15 g/L), magnesium sulfate (0.3 g/L), biotin (0.0013 g/L), yeast extract (4.9 g/L), glycerol (19.8 g/L), and trace elements.

Fermentation Conditions

Fermentation was carried out in three distinct phases. The first phase, batch phase, occurred in the cultivation media until carbon source exhaustion. At this point, fed-batch phase #1 was undertaken and consisted of pulse-addition of an aqueous solution containing 50% glycerol until an $OD_{600}$ 50 was achieved. Upon reaching of this OD, the fed-batch #2 induction phase was performed using L-arabinose (3 g/L in an aqueous 50% glycerol solution). Throughout the fed-batch phases, the % DO was maintained between 20-50% and the pH is controlled at pH 7.0 using ammonia hydroxide. The duration of the post induction phase was up to 48 hours.

Modification of Fermentation Induction Parameters for VB4-845 Expression

Initial fermentation conditions were predicated upon those implemented for the generation of other antibody molecules using a similar expression system ((Bosc and Manoosingh, 2007) WO2007/051315). Experiments directed at evaluating the impact of fermentation parameters on expression of original and optimized VB4-845 in the supernatant were carried out to identify conditions able to increase titers. Parameters were tested individually against the initial conditions, and the prominent ones able to increase expression were identified as: induction temperature, induction cell density, inducer concentration, and pH during the induction phase. The best condition identified for each parameter was combined to yield the "modified fermentation conditions" under which optimized VB4-845 was expressed and analyzed in the supernatant. Table 1 summarizes the changes to the conditions and the influence on the yield of VB4-845 when using the original (non-optimized) clone. These conditions were then re-tested and re-modified using the optimized VB4-845 clone. These results are summarized in Table 2. Tested parameters are indicated in bold.

Recipes

5 L of GMM Medium for Seed Culture

Ammonium sulfate ($(NH_4)_2SO_4$) (60±0.1 g), Potassium phosphate ($KH_2PO_4$) (7.85±0.05 g), Potassium phosphate ($K_2HPO_4$) (70.5±0.1 g), Magnesium sulfate ($MgSO_4$ Anhydrous) (1.4±0.1 g), Biotin (0.006±0.005 g), Yeast extract (23.0±0.1 g), Glycerol (92.5±0.1 g) and Phosphoric acid ($H_3PO_4$) (15±0.5 mL) were combined with RO water in a 5 L media bottle. The GMM medium was mixed for 30-45 minutes. RO water was added to a final volume of 5 L and mixed for an additional 5 minutes. The media was sterilized for 30 minutes using a liquid cycle.

Trace Element D Solution 1 L Batch

Ferric chloride ($FeCl_3.6H_2O$) (3.25±0.05 g), Zinc sulfate ($ZnSO_4.7H_2O$) (0.85±0.05 g), Manganese chloride ($MnCl_2.4H_2O$) (0.6±0.05 g), Sodium molybdate ($Na_2MoO_4.2H_2O$) (0.3±0.05 g), Cupric sulfate ($CuSO_4.5H_2O$) (0.12±0.02 g), Cobalt chloride ($CoCl_2.6H_2O$) (0.12±0.02 g), Boric acid ($H_3BO_3$) (0.36±0.05 g) and Phosphoric acid (conc. $H_3PO_4$) (48 mL) were combined with RO water and mixed for 20-30 minutes. The solution was poured into a 1 L measuring cylinder and RO water was added to a final volume of 1 L. The solution was placed in a 1 L bottle and stirred for an additional 5 minutes. The Trace element "D" solution was filtered using a 500 ml Nalgene 0.2 sterile bottle top filter into a sterile 1 L glass bottle. The bottle was wrapped in aluminum foil to avoid light exposure. The solution was stored at 2° C.-8° C. in a cold cabinet and used within 1 month from the date of preparation.

Nicotinic Acid Solution 500 mL

Nicotinic acid (5 g±0.1 g) was combined with RO water and mixed until it dissolved. The Nicotinic acid solution was poured into a 500 mL graduated cylinder and RO water was added to bring the final volume to 500 mL. The solution was stirred for 5 minutes before filtration. The Nicotinic Acid solution was poured into a sterile 1000 mL glass bottle via the 500 mL Nalgene 0.2 sterile bottle top filter. The vacuum line was attached to the filter. When filtration was complete, the filter was removed and the sterile cap was attached. The bottle was wrapped in aluminum foil to avoid exposure to light. The solution was stored at a refrigerated temperature (2-8° C.) for up to 1 month.

Calcium Chloride Solution 1 L

Calcium chloride dihydrate (100 g±0.1 g) was combined with RO water and mixed until it dissolved. The calcium chloride solution was poured into a 1 L graduated cylinder and RO water was added to bring the final volume to 1 L. The solution was stirred for 5 minutes before filtration. The calcium chloride solution was poured into the 500 mL Nalgene 0.2 sterile bottle top filter. The vacuum line was attached to the filter. When the filtration was completed, the filter was removed and the sterile cap was attached. The bottle was wrapped in aluminum foil to avoid exposure to light. The solution was stored at a refrigerated temperature (2-8° C.) for no longer than 1 month.

Thiamine-HCL 100 mL

Thiamine-HCl (10 g±0.1 g) was combined with RO and mixed until it dissolved. The Thiamine-HCl solution was poured into a 100 mL graduated cylinder and RO water was added to bring the final volume to 100 mL. The solution was stirred for 5 minutes before filtration. The Thiamine-HCl solution was poured into a sterile 250 ml glass bottle via the 500 ml Nalgene 0.2 sterile bottle top filter. The vacuum line was attached to the filter. When the filtration was complete, the filter was removed and the sterile cap was attached. The bottle was wrapped in aluminum foil to avoid exposure to light. The solution was stored at a refrigerated temperature (2-8° C.) for no longer than 1 month.

15 L of GMM Production Media

Ammonium sulfate ($(NH_4)_2SO_4$) (180±0.1 g), Potassium phosphate ($KH_2PO_4$) (23.55±0.05 g), Potassium phosphate ($K_2HPO_4$) (211.5±0.1 g), Magnesium sulfate ($MgSO_4$ Anhydrous) (4.2±0.1 g), Biotin (0.018±0.005 g), Yeast extract (69.0±0.1 g), Glycerol (277.5±0.1 g) and Phosphoric acid ($H_3PO_4$) (45±0.5 mL), P 2000 (2±0.1 mL) were combined with RO water and mixed for 20-30 minutes. The pH was adjusted to 7.0±0.2 (pH 6.8-7.2) with Ammonium hydroxide (50%). RO water was added to a final volume of 14 L. The 14 L GMM production medium was transferred to the fermenter and 2 mL of P 2000 was added directly into the fermentor with the medium. The medium was sterilized for 30 minutes in the 20 L Chemap fermenter. The DO probe was calibrated to 0% at least 10 minutes after the Start of the sterilization cycle. The GMM medium and the vessel were allowed to cool to 28° C. The temperature probe, DO probe, and pH probe were activated, the RPM was set to 300, and the airflow was set to 3 L/min. The medium was used within 72 hours of preparation.

3 L Batch for Feed 1

Glycerol (2100±0.5 g), Magnesium sulfate ($MgSO_4$ anhydrous) (30±0.1 g), Biotin (0.03±0.01 g), 10% Calcium chloride solution (105 mL), 10% Thiamine HCl solution (10.5 mL), 1% Nicotinic acid solution (21 mL) and RO water up to bring the volume to 3000 mL were used in the batch for Feed 1. 2100 g of glycerol was weighed into a clean 5 L media bottle. The magnesium sulfate was added to a clean 250 mL beaker containing 200 mL of RO water and mixed at a medium rate for 10 minutes. The biotin was weighed out and added to the magnesium sulfate solution, then mixed for 10 minutes. The magnesium sulfate/biotin solution was poured into the glycerol mixture. The beaker was rinsed with 150 mL of RO water and added to the glycerol mixture. RO water was added to a final volume of 3000 mL. The rest of the ingredients were aseptically added into the 5 L bottle and mixed for 30 minutes. The media was pumped through a sterile Sartibran P Filter into a 10 L storage bag.

5 L Batch for Feed#2

Glycerol (4375±1.0 g), Magnesium sulfate (MgSO$_4$) (62.5±0.1 g), Biotin (0.05±0.01 g), 10% Calcium chloride solution (175 mL), 10% Thiamine HCl solution (17.5 mL), 1% Nicotinic acid solution (35 mL) and L-arabinose 3% W/V (1000 mL) were used to prepare the batch for Feed#2.4375 g of glycerol was weighed out into a clean 10 L media bottle. The magnesium sulfate was weighed out and added to a clean 250 mL beaker containing 200 mL of RO water then placed on a magnetic stir plate and mixed at a medium rate for 10 minutes. The biotin was weighed out and added to the magnesium sulfate solution and mixed for 10 minutes. The magnesium sulfate/biotin solution was poured into the glycerol mixture. The beaker was rinsed with 150 mL of RO water and added to the glycerol mixture. 30 g of Arabinose was weighed out into a 1 L beaker and 700 ml of RO water was added and mixed for 30 minutes. The final volume was adjusted to 1.0 L using RO water. The Arabinose solution was poured into the 10 L bottle. The rest of the ingredients were aseptically added and stirred for 2 hours or until dissolved. The feed was pumped through a sterile Sartibran P Filter into a 10 L storage bag.

Seed Culture

A 2 mL volume from a frozen vial of cells from the master cell bank was used to inoculate 500 mL of GMM media containing 2.5 mL of a 0.5% tetracycline solution, 0.5 mL of a 10% CaCl$_2$ solution, 8.0 mL of a Trace element D solution, 1 mL of a 1% Nicotinic acid solution and 0.05 mL of a 10% Thiamine-HCL solution. The inoculum was allowed to grow for at least 18 hours before the optical density of the cells was checked. The seed culture was grown (200 rpm and 27±2° C.) to an OD between 2.0-2.5, at which point a volume equivalent to 1% of the production media volume of this seed culture was used to inoculate the production vessel.

Fed-Batch Fermentation

Pre-Induction

A 5 mL homogenous sample was aseptically withdrawn from the inoculum flask using 5 mL serological pipette. Using a micropipetter, 1.0 mL of the sample was pipetted into 4.0 mL of sterile GMM medium using a 5 mL pipette and stripettor. The OD$_{600}$ was measured on the spectrophotometer, which had been zeroed with sterile GMM medium. The OD value was multiplied by 5 to obtain the optical density of the cells in the shake-flask. When the OD value of the cells fell within specifications between 2.0-2.5, the fermentor was immediately inoculated with these cells.

A sample of the GMM media was withdrawn from the fermentor through the sampling port and the pH of the GMM media was measured. The pH probe was recalibrated on the fermentor to reflect the actual pH of the GMM media inside the fermentor. Ammonium hydroxide was added manually to the GMM media to adjust the pH of the fermentor to 7.0±0.2. The DO probe was calibrated to 100% as follows: (1) 150 mL of the seed culture was removed from the seed flask and the fermentor was inoculated with the remaining volume. (2) The pH of the remaining seed culture was measured. (3) A 25±10 mL sample was withdrawn from the fermentor and the OD$_{600}$ and pH were measured. (4) If the online pH deviated from the offline pH value by 0.05 then the online pH was re-calibrated to reflect the offline pH.

The initial reading of the culture was recorded and the cells were allowed to grow. When the % DO values reached 41%±1.0% the airflow was increased to 6 L/min and the RPM to 600. The % DO gradually increased then gradually decreased. When the dissolved oxygen of the culture reached 41%±1.0% again, the RPM was increased to 1000 and airflow to 10 L/min (maximum aeration). The % DO gradually decreased as the cells continued to grow. Once the carbon source was exhausted, the % DO started to increase rapidly. When the DO increased to >90%, feed 1 was started by adjusting the DO set-point to 40% and starting the feed pump for feed #1. The feed 1 intervals were monitored to ensure that the % DO was dropping below 40% so that feeding cycles could occur and so that the culture was not continuously feeding. If the % DO did not drop below 40% then the % DO set point was increased to +2% higher than the highest fluctuating % DO reading. The % DO set point was re-adjusted to lower values as necessary until 40% was reached. Approximately 25 mL of culture broth was removed at 90 minute intervals and the OD$_{600}$ nm of a 1/100 dilution was measured. The pH of the broth sample was also measured.

The growth, pH, % DO, and temperature of the culture were monitored. At an OD$_{600}$ of 50±1, Feed 1 was stopped and Feed 2 (contains 3.0% inducer L-arabinose) was started.

Induction Phase

Feed 2 was supplied to the culture over a 48 hour post induction period under the control of the dissolved oxygen controller. 25 mL of culture broth was removed at 0 hour post induction and 1 mL of culture broth was centrifuged for 15 minutes. The supernatant was stored in a −20° C. freezer. Approximately 25 mL of culture broth was removed every 8 hours and the OD$_{600}$ of a 1/200 dilution (0.5 mL in 99.5 mL RO water) post-induction broth sample was measured. The pH of the broth was also measured. Additionally, 1 mL of culture broth was centrifuged in a bench top centrifuge every 8 hours and the supernatant was stored in a −20° C. freezer.

Harvest

The culture was harvested 22-40 hours post induction. The fermentor was stopped and drained into a 20 L clean sterile tank then centrifuged at 8000 rpm for 30 minutes. The centrifuged supernatant was placed into a new clean sterile tank and the post fermentation yield was determined.

Modification of cultivation condition parameters including temperature, pH, inducer concentration, and culture density at time of induction in GMM media increased the expression levels of soluble VB4-845 in the culture supernatant by ~7-fold over that observed using the TB-based strategy when using the non-optimized VB4-845 clone. Utilization of the nucleotide sequence optimized VB4-845 clone in combination with the modified fermentation conditions increased the protein yields by another 2.5 to 4.5 fold and also resulted in a reduction in the time of induction required to reach maximal production.

Implementation of a combination of critical fermentation induction parameters raised expression levels of soluble VB4-845 in the culture supernatant to 17 to 31 fold higher as compared against the original fermentation conditions. (Table 3).

While the present application has been described with reference to what are presently considered to be the preferred examples, it is to be understood that the present application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Comparison of the expression levels of VB4-845 in the supernatant of E. coli cultures cultivated in either TB or GMM media using the non-optimized VB4-845 clone.

| Parameter | TB-based cultivation | GMM-based cultivation |
|---|---|---|
| Induction temperature | 25 ± 2° C. | 28 ± 2° C. |
| Inducer concentration | 167 g/L | 0.6 g/L |
| Induction cell density ($OD_{600}$) | 20 ± 5 | 50 ± 5 |
| pH | 7.15 ± 1 | 7.00 ± 1 |
| Induction time | 46 hours | 48 hours |
| VB4-845 titers | ~25 mg/L | ~170 mg/L |

* TB—Terrific Broth media; GMM—Glycerol Minimal Media

TABLE 2

Changes to Fermentation Conditions and Yields Using Optimized VB4-845 Clone

| | Original Clone and Conditions | Test #1 | Test #2 | Test #3 | Test #4 | Test #5 |
|---|---|---|---|---|---|---|
| Conditions | 15L | 15L | 2L | 2L | 2L | 2L |
| Media | TB | GMM | GMM | GMM | GMM | GMM |
| pH | 7.2 ± 1 | pH 7.0 ± 2 | pH 7.0 ± 2 | pH 7.0 | pH 7.0 | pH 7.0 |
| pH adjusted | no | yes | yes | yes | yes | yes |
| Temp | 25° C. ± 2° C. | 28° C. ± 1° C. | 28° C. ± 1° C. | 28° C. ± 1° C. | 28° C. ± 1° C. | 28° C. ± 1° C. |
| Feed 1 | 50% Glycerol | 50% Glycerol + additives | 50% Glycerol + additives | 50% Glycerol + additives | 50% Glycerol + additives | 50% Glycerol + additives |
| induction OD | 20 ± 5 | 50 ± 5 | 50 ± 5 | 50 ± 5 | 50 ± 5 | 100 ± 5 |
| Induction Feed | 50% Glycerol + 167 g/L arabinose | 50% Glycerol + additives + 6 g/L Arabinose | 50% Glycerol + additives + 6 g/L Arabinose | 50% Glycerol + additives + 3 g/L Arabinose | 50% Glycerol + additives + 0.6 g/L % Arabinose | 50% Glycerol + additives + 6 g/L Arabinose |
| Harvest | 48 hours post induction | 32-40 hours post induction | 32-40 hours post induction | 32-40 hours post induction | 32-40 hours post induction | 32-40 hours post induction |
| Yields | 21.7 mg/L | 439 mg/L | 544.71 mg/L | 458.28 mg/L | 94.58 mg/L | 154.28 mg/L |

| | Test #6 | Test #7 | Test #8 | Test #9 | Test #10 | Test #11 |
|---|---|---|---|---|---|---|
| Conditions | 2L | 2L | 2L | 2L | 2L | 2 L |
| Media | GMM | GMM | GMM | GMM | GMM | GMM |
| pH | pH 7.0 | pH 7.0 | pH 7.0 | pH 7.5 | pH 6.5 | pH 7.2 |
| pH adjusted | Yes | yes | yes | yes | yes | yes |
| Temp | 28° C. ± 1° C. | 26° C. ± 1° C. | 30° C. ± 1° C. | 28° C. ± 1° C. | 28° C. ± 1° C. | 28° C. ± 1° C. |
| Feed 1 | 50% Glycerol + additives | 50% Glycerol + additives | 50% Glycerol + additives | 50% Glycerol + additives | 50% Glycerol + additives | 50% Glycerol + additive |
| induction OD | 25 ± 5 | 50 ± 5 | 50 ± 5 | 50 ± 5 | 50 ± 5 | 50 ± 5 |
| Induction Feed | 50% Glycerol + additives + 6 g/L Arabinose | 50% Glycerol + additives + 6 g/L Arabinose | 50% Glycerol + additives + 6 g/L Arabinose | 50% Glycerol + additives + 6 g/L Arabinose | 50% Glycerol + additives + 6 g/L Arabinose | 50% Glycerol + additives + 6 g/L Arabinose |
| Harvest | 32-40 hours post induction | 32-40 hours post induction | 32-40 hours post induction | 32-40 hours post induction | 32-40 hours post induction | 22 hours post induction |
| Yields | 71.37 mg/L | 145 mg/L | 394 mg/L | 190.87 mg/L | too low to quantify | 790 mg/L |

TABLE 3

Expression levels of VB4-845 in the supernatant of *E. coli* cultures cultivated in either TB or GMM media using either native or optimized clones with original or modified fermentation conditions.

| Clone type | Non-Optimized Clone | | Optimized clone |
|---|---|---|---|
| Media type | TB | GMM | GMM |
| VB4-845 titers in culture broth | 25 mg/L | 170 mg/L | 145-790 mg/L |
| Induction temperature | 25 ± 2° C. | 28 ± 2° C. | 26-30 ± 1° C. |
| Inducer concentration | 167 g/L | 0.6 g/L | 3-6 g/L |
| Induction cell density ($OD_{600}$) | 20 ± 5 | 50 ± 5 | 50 ± 5 |
| pH | 7.15 ± 1 | 7.00 ± 1 | 7-7.5 ± 1.5 |
| Induction time | 46 hours | 48 hours | 22-40 hours |

REFERENCE LIST

Baldari, C., Murray, J. A., Ghiara, P., Cesareni, G., and Galeotti, C. L. (1987). A novel leader peptide which allows efficient secretion of a fragment of human interleukin 1 beta in *Saccharomyces cerevisiae*. EMBO J. 6, 229-234.

Baneyx, F., Ayling, A., Palumbo, T., Thomas, D., and Georgiou, G. (1991). Optimization of growth conditions for the production of proteolytically-sensitive proteins in the periplasmic space of *Escherichia coli*. Appl. Microbiol. Biotechnol. 36, 14-20.

Bosc, D. and Manoosingh, D. METHODS AND PROCESSES OF CONTROLLING FERMENTATION. Viventia Biotech. WO27051315A1. May 10, 2007. Nov. 7, 2006.
Ref Type: patent Brinster, R. L., Chen, H. Y., Trumbauer, M. E., Yagle, M. K., and Palmiter, R. D. (1985). Factors affecting the efficiency of introducing foreign DNA into mice by microinjecting eggs. Proc Natl. Acad. Sci. U.S.A 82, 4438-4442.

Chahal, F. C., MacDonald G. C, and Cizeau, J. Novel Cancer Associated Antigen. Viventia Biotech. WO07071051A 1. Jun. 28, 2007.
Ref Type: patent Cullen, D., Gray, G. L., Wilson, L. J., Hayenga, K. J., Lamsa, M. H., Rey, M. W., Norton, S., and Berka, R. M. (1987). Controlled Expression and Secretion of Bovine Chymosin in *Aspergillus Nidulans*. Nat Biotech 5, 369-376.

Demeure, M. J., Damsky, C. H., Elfman, F., Goretzki, P. E., Wong, M. G., and Clark, O. H. (1992). Invasion by cultured human follicular thyroid cancer correlates with increased beta 1 integrins and production of proteases. World J Surg. 16, 770-776.

Endo, S., Tomimoto, Y., Shimizu, H., Taniguchi, Y., and Onizuka, T. (2006). Effects of *E. coli* Chaperones on the Solubility of Human Receptors in an In Vitro Expression System. Mol. Biotechnol. 33, 199-210.

Gennaro, A. R. (2000). Remington's Pharmaceutical Sciences. (Easton, Pa.: Mack Publishing Company).

Glover, N., MacDonald G. C, Cizeau, J, Entwistle, J., and Chahal, F. C. Cancer Specific Antibody and Cell Surface Proteins. Viventia Biotech.
WO06066408A1. Jun. 29, 2006.
Ref Type: patent Glover, N., MacDonald G. C, Entwistle, J., Cizeau, J, Bosc, D, and Chahal, F. C. Tumor Specific Antibody. Viventia Biotech. WO0512134A1. Dec. 22, 2005. Jun. 10, 2005.
Ref Type: patent Goeddel, D. V. (1990). Systems for heterologous gene expression. Methods Enzymol. 185, 3-7.

Hammer, R. E., Brinster, R. L., Rosenfeld, M. G., Evans, R. M., and Mayo, K. E. (1985). Expression of human growth hormone-releasing factor in transgenic mice results in increased somatic growth. Nature 315, 413-416.

Hinnen, A., Hicks, J. B., and Fink, G. R. (1978). Transformation of yeast. Proc Natl. Acad. Sci. U.S.A 75, 1929-1933.

Ito, H., Fukuda, Y., Murata, K., and Kimura, A. (1983). Transformation of intact yeast cells treated with alkali cations. J. Bacteriol. 153, 163-168.

Kaufman, R. J., Murtha, P., and Davies, M. V. (1987). Translational efficiency of polycistronic mRNAs and their utilization to express heterologous genes in mammalian cells. EMBO J. 6, 187-193.

Kurjan, J. and Herskowitz, I. (1982). Structure of a yeast pheromone gene (MF alpha): a putative alpha-factor precursor contains four tandem copies of mature alpha-factor. Cell 30, 933-943.

Leder, P. and Stewart, T. A. Transgenic Non Human Mammals. President and Fellows of Harvard College. [U.S. Pat. No. 4,736,866], 1-8. Apr. 12, 1988. US. Jun. 22, 1984.
Ref Type: patent Luckow, V. A. and Summers, M. D. (1989). High level expression of nonfused foreign genes with *Autographa californica* nuclear polyhedrosis virus expression vectors. Virology 170, 31-39.

Mackay, A. R., Gomez, D. E., Nason, A. M., and Thorgeirsson, U. P. (1994). Studies on the effects of laminin, E-8 fragment of laminin and synthetic laminin peptides PA22-2 and YIGSR on matrix metalloproteinases and tissue inhibitor of metalloproteinase expression. Lab Invest 70, 800-806.

Makrides, S. C. (1996). Strategies for achieving high-level expression of genes in *Escherichia coli*. Microbiol. Rev. 60, 512-538.

Moore, D. H., Allison, B., Look, K. Y., Sutton, G. P., and Bigsby, R. M. (1997). Collagenase expression in ovarian cancer cell lines. Gynecol. Oncol 65, 78-82.

Palmiter, R. D. and Brinster, R. L. (1985). Transgenic mice. Cell 41, 343-345.

Palmiter, R. D., Norstedt, G., Gelinas, R. E., Hammer, R. E., and Brinster, R. L. (1983). Metallothionein-human GH fusion genes stimulate growth of mice. Science 222, 809-814.

Sambrook, J., MacCallum, P., and Russell, D. (2001). Molecular Cloning: A Laboratory Manual. Cold Spring Harbor Laboratory Press).

Schneider, J. C., Chew, L. C., Badgley, A. K., and Ramseier, T. M. Protein expression systems. Dow Global Technologies. US2004000994138, 1-75. 2005. US. Aug. 25, 2005.
Ref Type: patent Schultz, L. D., Tanner, J., Hofmann, K. J., Emini, E. A., Condra, J. H., Jones, R. E., Kieff, E., and Ellis, R. W. (1987). Expression and secretion in yeast of a 400-kDa envelope glycoprotein derived from Epstein-Barr virus. Gene 54, 113-123.

Seed, B. (1987). An LFA-3 cDNA encodes a phospholipid-linked membrane protein homologous to its receptor CD2. Nature 329, 840-842.

Shi, Y. E., Torri, J., Yieh, L., Wellstein, A., Lippman, M. E., and Dickson, R. B. (1993). Identification and characterization of a novel matrix-degrading protease from hormone-dependent human breast cancer cells. Cancer Res 53, 1409-1415.

Sinkar, V. P., White, F. F., and Gordon, M. P. (1987). Molecular Biology of the RI Plasmid—A Review. J. Biosci. 11, 47-57.

Smith, G. E., Summers, M. D., and Fraser, M. J. (1983). Production of human beta interferon in insect cells infected with a baculovirus expression vector. Mol. Cell. Biol. 3, 2156-2165.

Spiess, E., Bruning, A., Gack, S., Ulbricht, B., Spring, H., Trefz, G., and Ebert, W. (1994). Cathepsin B activity in human lung tumor cell lines: ultrastructural localization, pH sensitivity, and inhibitor status at the cellular level. J Histochem. Cytochem. 42, 917-929.

Thompson, E. W., Yu, M., Bueno, J., Jin, L., Maiti, S. N., Palao-Marco, F. L., Pulyaeva, H., Tamborlane, J. W., Tirgari, R., Wapnir, I., and (1994). Collagen induced MMP-2 activation in human breast cancer. Breast Cancer Res Treat. 31, 357-370.

Vasseur-Godbillon, C., Hamdane, D., Marden, M. C., and Baudin-Creuza, V. (2006). High-yield expression in *Escherichia coli* of soluble human alpha-hemoglobin complexed with its molecular chaperone. Protein Eng Des Sel 19, 91-97.

Xu, H. M., Zhang, G. Y., Ji, X. D., Cao, L., Shu, L., and Hua, Z. C. (2005). Expression of soluble, biologically active recombinant human endostatin in *Escherichia coli*. Protein Expr. Purif. 41, 252-258.

Young, T. N., Rodriguez, G. C., Rinehart, A. R., Bast, R. C., Jr., Pizzo, S. V., and Stack, M. S. (1996). Characterization of gelatinases linked to extracellular matrix invasion in ovarian adenocarcinoma: purification of matrix metalloproteinase 2. Gynecol. Oncol 62, 89-99.

Zambryski, P., Herrerra-Estrella, L., DeBlock, M., and Van Montagu, M. (1984). In Genetic Engineering: Principles and Methods, J. Setlow and A. Hollaender, eds. (New York, N.Y.: Plenum Press), pp. 253-278.

Zangemeister-Wittke, U. and Di Paolo, C. Methods for Treating Cancer Using an Improved Immunotoxin. University of Zurich. WO06087196A2. Aug. 24, 2006. Feb. 16, 2006.
Ref Type: patent Zangemeister-Wittke, U., Di, Paolo C., Tschudi, D. C., Glover, N. R., and Fitsialos, D. P. Methods for Treating Cancer Using an Immunotoxin. PCT/CA2004/000637, 1-51. 2006. WO.
Ref Type: patent Zhang, Z., Gildersleeve, J., Yang, Y. Y., Xu, R., Loo, J. A., Uryu, S., Wong, C. H., and Schultz, P. G. (2004). A new strategy for the synthesis of glycoproteins. Science 303, 371-373.

---

We claim:

1. An isolated nucleic acid sequence comprising the $V_L$ region shown in SEQ ID NO:5.

2. An isolated nucleic acid sequence comprising the $V_H$ region shown in SEQ ID NO:7.

3. An isolated nucleic acid sequence encoding an immunoconjugate and comprising the nucleic acid sequence shown in SEQ ID NO:3.

4. An isolated nucleic acid sequence encoding an immunoconjugate and comprising the nucleic acid sequence shown in SEQ ID NO:9.

5. An expression vector comprising a nucleic acid sequence according to claim 1.

6. An expression vector comprising a nucleic acid sequence according to claim 2.

7. An expression vector comprising a nucleic acid sequence according to claim 3.

8. An expression vector comprising a nucleic acid sequence according to claim 4.

9. An isolated host cell comprising the expression vector of claim 5.

10. An isolated host cell comprising the expression vector of claim 6.

11. An isolated host cell comprising the expression vector of claim 7.

12. An isolated host cell comprising the expression vector of claim 8.

13. The host cell according to claim 9 wherein the host cell is *E. coli*.

14. The host cell according to claim 10 wherein the host cell is *E. coli*.

15. The host cell according to claim 11 wherein the host cell is *E. coli*.

16. The host cell according to claim 12 wherein the host cell is *E. coli*.

17. A method of expressing a recombinant protein, comprising the steps:
    culturing the host cell according to claim 9 encoding a recombinant protein comprising the amino acid sequence encoded by SEQ ID NO:5 and
    inducing expression of said recombinant protein, wherein the recombinant protein is expressed.

18. A method of expressing a recombinant protein, comprising the steps:
    culturing the host cell according to claim 10 encoding a recombinant protein comprising the amino acid sequence encoded by SEQ ID NO:7 and
    inducing expression of said recombinant protein, wherein the recombinant protein is expressed.

19. A method of expressing a recombinant protein, comprising the steps:
    culturing the host cell according to claim 11 encoding a recombinant protein comprising the amino acid sequence encoded by SEQ ID NO:3 and
    inducing expression of said recombinant protein, wherein the recombinant protein is expressed.

20. A method of expressing a recombinant protein, comprising the steps:
    culturing the host cell according to claim 12 encoding a recombinant protein comprising the amino acid sequence encoded by SEQ ID NO:9 and
    inducing expression of said recombinant protein, wherein the recombinant protein is expressed.

21. The method of claim 17 wherein the recombinant protein is a binding protein.

22. The method of claim 18 wherein the recombinant protein is a binding protein.

23. The method of claim 17, wherein the host cell is *E. coli*.

24. The method of claim 18, wherein the host cell is *E. coli*.

25. The method of claim 19, wherein the host cell is *E. coli*.

26. The method of claim 20, wherein the host cell is *E. coli*.

* * * * *